(12) United States Patent
Isobe et al.

(10) Patent No.: US 11,454,587 B2
(45) Date of Patent: Sep. 27, 2022

(54) MEASUREMENT APPARATUS, MEASUREMENT METHOD, AND PROGRAM

(71) Applicant: Sony Semiconductor Solutions Corporation, Kanagawa (JP)

(72) Inventors: Hiroshi Isobe, Kanagawa (JP); Hidetoshi Kabasawa, Tokyo (JP); Ichiro Ujiie, Kanagawa (JP); Tomonori Masuno, Kanagawa (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 348 days.

(21) Appl. No.: 16/757,010

(22) PCT Filed: Sep. 20, 2019

(86) PCT No.: PCT/JP2019/037020
§ 371 (c)(1),
(2) Date: Apr. 17, 2020

(87) PCT Pub. No.: WO2020/075480
PCT Pub. Date: Apr. 16, 2020

(65) Prior Publication Data
US 2020/0340911 A1 Oct. 29, 2020

(30) Foreign Application Priority Data
Oct. 12, 2018 (JP) .............................. JP2018-193178

(51) Int. Cl.
*G01J 3/02* (2006.01)
*G01N 21/25* (2006.01)
(Continued)

(52) U.S. Cl.
CPC .......... *G01N 21/251* (2013.01); *A01D 46/30* (2013.01); *A01G 3/02* (2013.01); *G01J 3/36* (2013.01); *G01N 33/025* (2013.01)

(58) Field of Classification Search
CPC .. G01N 21/251; G01N 33/025; G01N 21/314; G01N 21/3554; A01D 46/30; A01G 3/02; G01J 3/36; G01D 21/00; G06T 7/00
See application file for complete search history.

(56) References Cited

U.S. PATENT DOCUMENTS

2015/0173297 A1 6/2015 Pitzer
2015/0262414 A1* 9/2015 Minato ................ G06V 10/757
345/420
(Continued)

FOREIGN PATENT DOCUMENTS

CN 101121167 A 2/2008
CN 103143508 A 6/2013
(Continued)

OTHER PUBLICATIONS

Extended European Search Report dated Nov. 11, 2020 for corresponding European Application No. 19870052.8.
(Continued)

*Primary Examiner* — Abdullahi Nur
(74) *Attorney, Agent, or Firm* — Michael Best & Friedrich LLP

(57) ABSTRACT

In a measurement apparatus or a measurement method, an information processing apparatus executes: a process of specifying a bunch of grapes to be measured on the basis of detection of grasping of the bunch of grapes by a gripper; and a process of starting to measure the number of pieces of the specified bunch of grapes.

22 Claims, 19 Drawing Sheets

(51) Int. Cl.
*A01D 46/30* (2006.01)
*A01G 3/02* (2006.01)
*G01J 3/36* (2006.01)
*G01N 33/02* (2006.01)

(56) References Cited

U.S. PATENT DOCUMENTS

| | | | |
|---|---|---|---|
| 2016/0155235 A1* | 6/2016 | Miyatani | G06V 10/443 382/103 |
| 2018/0129894 A1 | 5/2018 | Nuske et al. | |
| 2018/0158207 A1 | 6/2018 | Germain et al. | |

FOREIGN PATENT DOCUMENTS

| | | |
|---|---|---|
| CN | 105738294 A | 7/2016 |
| CN | 106111556 A | 11/2016 |
| ES | 2470065 | 6/2014 |
| JP | 01-312447 A | 12/1989 |
| JP | 2003000031 A | 1/2003 |
| JP | 2003-143960 A | 5/2003 |
| JP | 2012-133665 A | 7/2012 |
| JP | 2016-057738 A | 4/2016 |

OTHER PUBLICATIONS

Jimenez A R et al., "Automatic fruit recognition: a survey and new results using Range/Attenuation images", Pattern Recognition, Elsevier, GB, vol. 32, No. 10, Oct. 1, 1999 (Oct. 1, 1999), pp. 1719-1736, XP004171577, ISSN: 0031-3203, DOI: 10.1016/S0031-3203(98)00170-8 * p. 1725, col. 1, paragraph figures 4-6.

Xiong Juntao et al., "Visual positioning technology of picking robots for dynamic litchi clusters with disturbance", Computers and Electronics in Agriculture, Elsevier, Amsterdam, NL, vol. 151, Jun. 15, 2018 (Jun. 15, 2018), pp. 226-237, XP085417105, ISSN: 0168-1699, DOI: 10.1016/J.COMPAG.2018.06.007 * figures 1-2, 6, 12.

* cited by examiner

A

B

C

D

A

B

MEASUREMENT APPARATUS, MEASUREMENT METHOD, AND PROGRAM

TECHNICAL FIELD

The present technique relates to a measurement apparatus, a measurement method, and a program, and particularly, to a technique that can be used to measure a feature amount of an object to be measured in the course of various types of work.

BACKGROUND ART

Various techniques are known in relation to measurement of an object.

For example, PTL 1 described below discloses a technique of using a linear image sensor to scan grains of rice flowing on a belt conveyor to assess the quality.

CITATION LIST

Patent Literature

[PTL 1]
Japanese Patent Laid-Open No. 1989(H01)-312447

SUMMARY

Technical Problem

For example, considering a case of measuring the number, the size, and the like regarding an object to be measured, it is important to specify the object to be measured first.

However, it is not preferable to require a worker to perform some extra action in order to just specify the object to be measured.

Therefore, an object of the present technique is to enable to appropriately specify an object to be measured without imposing an extract load of action or load of operation on a user (worker) in the course of work involving measurement performed by a measurement apparatus.

Solution to Problem

A measurement apparatus according to the present technique includes: a measurement object specification unit that executes a process of specifying an object to be measured on the basis of detection of grasping of an object by a gripper; and a measurement unit that obtains a measurement result in a measurement process of a feature amount of the object to be measured specified by the measurement object specification unit.

The gripper is, for example, a thing that can grasp the object, such as hands or fingers of a worker, hands or fingers of the worker wearing gloves or a predetermined tool, a tool that can grasp the object through operation by a person, a tool that can automatically grasp the object, and a robot arm.

The object denotes various objects, such as crops like grapes, bananas, or tomatoes, natural objects like trees or animals, and industrial products, and the object to be measured is all or part of the objects specified by grasping.

The feature amount denotes a value that can be quantified, compared, and evaluated, such as the number of pieces, dimension (size), color, component content, component ratio, sugar content, moisture content, and estimated price.

The measurement apparatus according to the present technique can further include a presentation control unit that executes a process for presentation based on the measurement result.

That is, the presentation control unit performs control to use display, sound, vibration, or the like to present the feature amount measured by the measurement unit or information based on the feature amount. For example, the presentation control unit executes a process of presenting measurement information, determination information based on the measurement information, or the like.

In the measurement apparatus according to the present technique, the measurement process can be executed by using a captured image.

For example, an image of the object captured by an integrated or separate imaging apparatus is input. The captured image is used to measure the feature amount that can be determined from the image.

In the measurement apparatus according to the present technique, the measurement process can be executed on the basis of detection of grasping of the object by the gripper.

That is, the measurement of the feature amount of the object to be measured is started by the detection of the grasping of the object by the gripper.

In the measurement apparatus according to the present technique, the measurement process can be executed on the basis of detection of grasping of the object and moving of the object by the gripper.

For example, the measurement of the feature amount of the object to be measured is started when some motion is applied to the object in the grasped state. The movement can be shaking, holding and moving up, down, left, right, back, and forth, rotating, or the like.

In the measurement apparatus according to the present technique, the measurement process can be executed on the basis of detection of grasping of the object by the gripper and a predetermined action other than the grasping.

For example, a predetermined action in the state in which the gripper grasps the object is detected to start the measurement of the feature amount of the object to be measured. The predetermined action can be an audio action, such as a speech of the worker and generation of a predetermined sound, a gesture action by the hand of the worker or by equipment (such as scissors), or the like.

In the measurement apparatus according to the present embodiment, the measurement process is executed by using images of a plurality of frames captured in a period in which the object to be measured is moved.

For example, the captured images of the object imaged by the integrated or separate imaging unit are input, and a plurality of frames of the images obtained as, for example, moving images are used to perform the measurement.

In the measurement apparatus according to the present technique, the measurement object specification unit can set, as the object to be measured, the object grasped and moved by the gripper.

For example, the measurement object specification unit sets, as the object to be measured, an object or part of the object applied with some motion in the grasped state. Examples of the movement include holding the object to move the object up, down, left, right, back, and forth, shaking the object, rotating the object, and the like.

The measurement apparatus according to the present technique can further include a target setting unit that sets a target value of the feature amount, in which the target setting unit obtains a difference value of the feature amount measured in the measurement process and the target value.

For example, the target value of the feature amount is set and stored on the basis of user settings, automatic settings, or the like to allow comparing the target value and the measurement value.

The measurement apparatus according to the present technique can further include a presentation control unit that executes a process for presenting the difference value.

The presentation control unit uses a method of display, sound, or the like to present the difference between the current feature amount and the target value.

In the measurement apparatus according to the present technique, the movement can be a rotational movement.

For example, the rotation of the object in the grasped state is detected to start the measurement.

In the measurement apparatus according to the present technique, the gripper can be one of a hand of a person, a tool operated by the person, and an automatically operated robot arm.

The measurement object specification unit detects grasping of the object by one of the hand of the person, the tool, and the robot arm as the gripper to specify the object to be measured. Examples of the hand of the person include a bare hand and a hand wearing a glove or the like. The tool denotes any tool that can be grasped by the intention of the person regardless of the mode, such as a tool operated by the person by hand, a tool operated by something other than the hand, a tool mounted on the hand and used, and a remotely controlled tool. The robot arm denotes a robot arm that can be grasped by automatic control.

In the measurement apparatus according to the present technique, the object as the object to be measured can be a crop.

That is, the measurement object specification unit specifies grasped individual crops as the object to be measured among the crops. The crops mentioned here are crops in a broad sense including fruits, vegetables, grains, trees, flowers, mushrooms, fertilizers, animal feed, garden crops, industrial crops, and the like.

In the measurement apparatus according to the present technique, the measurement object specification unit can execute a process of setting, as the object to be measured, a bunch of grapes in which a branch is grasped by the gripper, and in the measurement process, the number of pieces can be measured as the feature amount of the bunch of grapes set as the object to be measured.

The bunch of grapes in which the branch is held is set as the object to be measured, and the number of pieces of the bunch is measured.

The measurement apparatus according to the present technique can further include an imaging unit that captures an image to be used in the measurement process.

For example, an integrated or separate imaging unit is included.

The measurement apparatus according to the present technique can further include an imaging unit that captures an image to be used in the measurement process, and a presentation unit that presents the measurement result, in which the imaging unit and the presentation unit are arranged on a body-mounted unit.

The body-mounted unit is a unit that can be mounted on the body of a person or on clothes. For example, the body-mounted unit can be a head-mounted type, an eyeglass type, an earphone type, a wristband type, a clothes type, a clip type, a pocket storage type, a pendant type, or the like. The imaging unit and the presentation unit are arranged on the body-mounted unit.

The presentation unit denotes a unit that can present the measurement result to the user and denotes a unit, such as, for example, a display unit, a sound output unit, and a vibration unit, that can present some information to the five senses of the user.

In the measurement apparatus according to the present technique, the presentation unit can be a display unit that displays information on a display surface arranged in front of eyes of a user.

For example, information, such as a measurement result, is displayed on the display unit that is a head-mounted type, an eyeglass type, or the like and that is arranged in front of the eyes of the user.

In the measurement apparatus according to the present technique, a sensor unit that detects the grasping of the object by the gripper can be provided.

Examples of the sensor unit that detects grasping of the object by the gripper, such as the hand of the person, the tool, and the robot arm, include an imaging apparatus, a pressure sensor, a thermo tracer, a distance measurement sensor, and the like that detect an image, pressure, temperature information, distance measurement information, and the like.

A measurement method according to the present technique is executed by an information processing apparatus, the measurement method including: a process of specifying an object to be measured on the basis of detection of grasping of an object by a gripper; and a process of obtaining a measurement result in a measurement process of a feature amount of the specified object to be measured. That is, the information processing apparatus realizes an appropriate specification process of the object to be measured.

A program according to the present technique is a program causing an information processing apparatus to execute: the process of specifying the object to be measured; and the process of obtaining the measurement result. This realizes an information processing apparatus that can specify the object to be measured.

In addition, a measurement method according to the present technique is executed by an information processing apparatus, the measurement method including: a process of specifying a bunch of grapes to be measured on the basis of detection of grasping of the bunch of grapes by a gripper; and a process of starting to measure the number of pieces of the specified bunch of grapes.

Alternatively, an information processing apparatus executes: a process of specifying a bunch of grapes grasped by a gripper; and a process of measuring the number of pieces of the specified bunch of grapes along with rotation of the specified bunch of grapes.

DESCRIPTION OF EMBODIMENTS

Hereinafter, embodiments will be described in the following order.
<1. Configuration Example of Measurement Apparatus>
<2. Processing Example of First Embodiment>
<3. Processing Example of Second Embodiment>
<4. Processing Example of Third Embodiment>
<5. Processing Example of Fourth Embodiment>
<6. Processing Example of Fifth Embodiment>
<7. Examples of Apparatus and System Configuration>
<8. Conclusion and Modifications>

1. Configuration Example of Measurement Apparatus

In embodiments, a measurement apparatus that can measure the number of pieces in a bunch of grapes and the like as described later will be illustrated as an example of a measurement apparatus used by a grape farmer. However, the usage is obviously not limited to this.

Figure 1:
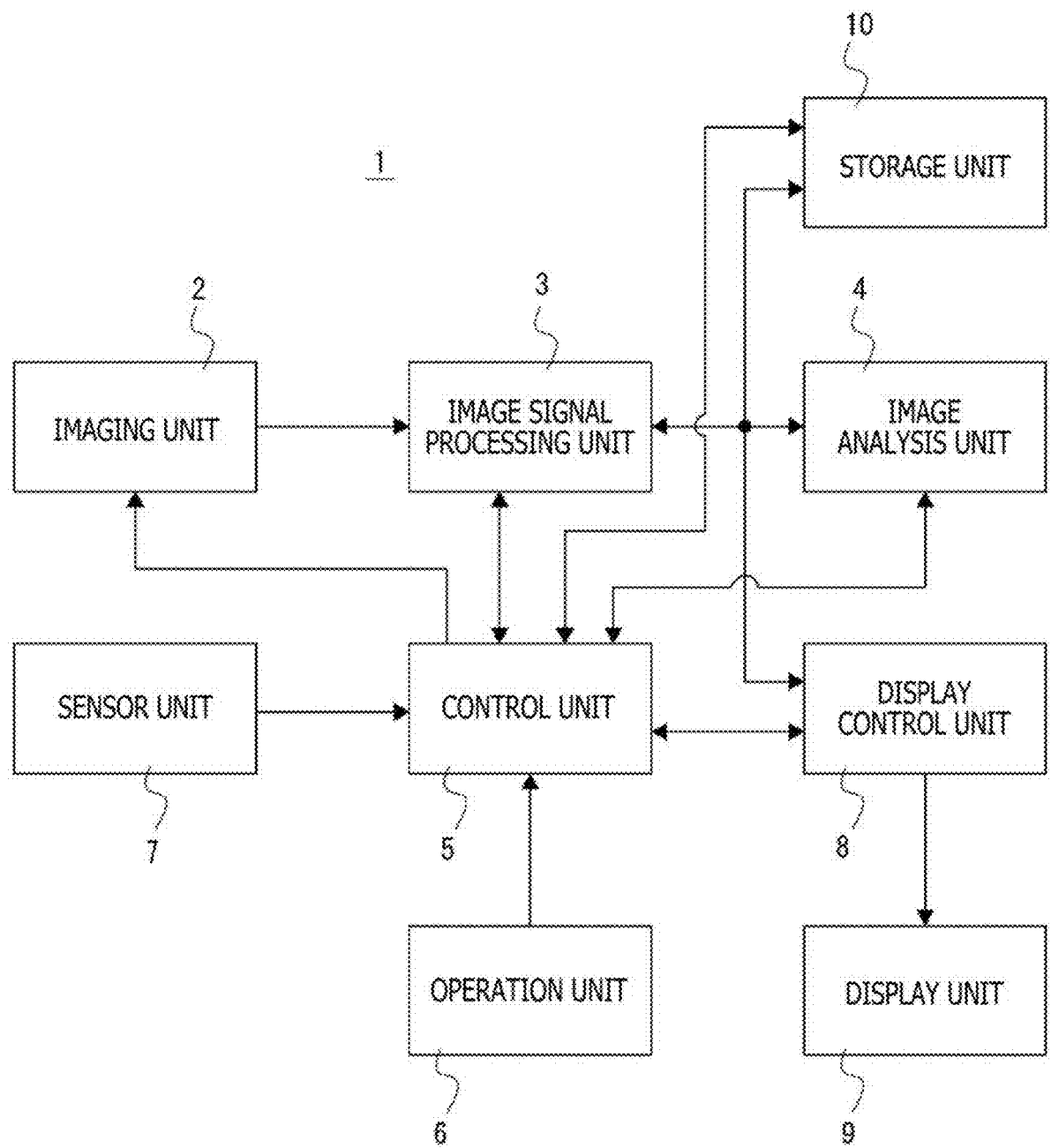
FIG. 1 is a block diagram of a measurement apparatus in embodiments of the present technique.

FIG. 1 illustrates a configuration example of a measurement apparatus 1 in the embodiments.

The measurement apparatus 1 in the example includes an imaging unit 2, an image signal processing unit 3, an image analysis unit 4, a control unit 5, an operation unit 6, a sensor unit 7, a display control unit 8, a display unit 9, and a storage unit 10.

The imaging unit 2 can image an object to be measured, such as grapes being cultivated in a grape farm.

Specifically, the imaging unit 2 can be a normal visible light camera that obtains at least an object image or a camera with a distance measurement function for measuring the distance to a subject. The camera with the distance measurement function can be a camera provided with an image sensor for capturing an image and also provided with an image sensor for detection in a distance measurement method based on, for example, an STL (Structured Light) system or a ToF (Time of Flight) system or can be a stereo camera.

In addition, depending on the feature amounts to be measured or the usage, the imaging unit 2 can be a camera, such as a near infrared camera, a multispectral camera, and a specific wavelength imaging camera, including an image sensor with specialized wavelength that captures an image for measurement.

Furthermore, the imaging unit 2 may be a thermo tracer that captures a temperature distribution image.

The image sensor mounted on the imaging unit 2 is, for example, an imaging element, such as a CCD (Charge Coupled Device) sensor and a CMOS (Complementary Metal Oxide Semiconductor) sensor, that receives light from a subject entering through an imaging optical system in the imaging unit 2, converts the light into an electrical signal, and outputs the electrical signal. The image sensor can be a sensor driven by a global shutter system or a rolling shutter system.

The image sensor applies, for example, a CDS (Correlated Double Sampling) process, an AGC (Automatic Gain Control) process, and the like to the electrical signal obtained by photoelectric conversion of the received light and further executes an A/D (Analog/Digital) conversion process. The image sensor then outputs an image signal as digital data to the image signal processing unit 3 of a later stage.

The image signal processing unit 3 includes, for example, an image processing processor including a DSP (Digital Signal Processor) or the like. The image signal processing unit 3 applies various processes to the image signal as digital data input from the imaging unit 2.

For example, in the case of an image signal of a normal visible light image, the image signal processing unit 3 executes a clamping process of clamping the black level of R (red), G (green), and B (blue) at a predetermined level, a correction process between color channels of R, G, and B, a demosaicing process of including color components of all of R, G, and B in the image data of each pixel, a process of generating (separating) a luminance (Y) signal and a color (C) signal, and the like.

Furthermore, the image signal processing unit 3 may also apply a necessary resolution conversion process, such as resolution conversion for recording, for communication output, or for monitor image, to the image signal subjected to various types of signal processing.

In addition, the image signal processing unit 3 may also apply, for example, a compression process, an encoding process, or the like for recording or for communication to the image data subjected to the resolution conversion.

The image analysis unit 4 extracts a frame of an image signal subjected to a predetermined process executed by the image signal processing unit 3 and executes an image analysis process for measurement. For example, the image analysis unit 4 uses a method, such as pattern matching, to determine the type and the operation state of an object as a subject, determines the area and the attributes of the object for measuring the feature amounts, or performs a measurement based on the determination.

The image analysis unit 4 executes a process of setting each frame (or intermittent frames) in video filming as a processing target and analyzing the frame to determine the situation on the subject side or to obtain information for the determination. For example, the image analysis unit 4 determines the situation regarding the gripper and the object or calculates information for determining the state of grasping or the like. Furthermore, the image analysis unit 4 may measure the feature amounts from the frame during imaging.

In addition, the image analysis unit 4 can read the image data captured by the imaging unit 2 and stored in the storage unit 10 and set the image data as a processing target to perform an analysis regarding the object as a subject, such as measurement of the feature amounts and calculation of information for the measurement.

The information determined by the image analysis unit 4 is supplied to the control unit 5 and used in a series of processes for measurement.

Note that the image analysis unit 4 may include an AI (artificial intelligence) engine and may be able to execute an image recognition process based on machine learning, deep learning, or the like to recognize, for example, the determination of the object, the state of the gripper, and the like or to recognize the part regarding the measurement of the feature amounts.

The control unit 5 includes a microcomputer (arithmetic processing apparatus) including a CPU (Central Processing Unit), a ROM (Read Only Memory), a RAM (Random Access Memory), a flash memory, and the like.

The CPU executes a program stored in the ROM, the flash memory, or the like to comprehensively control the entire measurement apparatus 1.

The RAM is used as a working area in various types of data processing of the CPU and is used to temporarily store data, programs, and the like.

The ROM and the flash memory (non-volatile memory) are used for storing an OS (Operating System) used by the CPU to control each component and for storing content files, such as image files, as well as application programs for various operations, firmware, and the like.

The control unit 5 performs control regarding the imaging operation, such as shutter speed, exposure adjustment, and frame rate, in the imaging unit 2, parameter control of various types of signal processing in the image signal processing unit 3, and control of the analysis process of the image analysis unit 4. In addition, the control unit 5 executes a setting process, imaging operation control, a measurement process, display operation control, and the like corresponding to the operation of the user.

Note that the control unit 5 may have the functions of the image analysis unit 4.

The operation unit 6 can be a controller, such as a key, a switch, and a dial, a touch panel, or the like provided on the housing of the apparatus. Depending on the operation unit 6, the user can perform, for example, a power on/off operation, various setting operations, an input operation of a target value, an activation of a program, and the like. The operation unit 6 transmits a signal corresponding to the input operation to the control unit 5.

Note that, in the present embodiments, an operation for specifying the object to be measured (for example, specifying the bunch of grapes as a measurement object) or an operation as a measurement start trigger (measurement start operation of the number of pieces) is an operation not performed by the operation unit 6 in order to prevent direct operations by the user as described later. However, the operation unit 6 may be able to perform the operations.

The sensor unit 7 represents various sensors as a whole provided as necessary. For example, the sensor unit 7 can include various sensors, such as a pressure sensor, a sound sensor, a position sensor, an illuminance sensor, a contact sensor, a temperature sensor, a distance measurement sensor, an acceleration sensor, an angular velocity sensor, a pressure sensor, an altitude sensor, a weight sensor, and a body status sensor that detects the pulse, the body temperature, and the like, and the sensor unit 7 can include sensors necessary for the process to be adopted for measurement.

The various sensors perform sensing for measuring the feature amounts, sensing for specifying the object to be measured, sensing for determining the start of measurement (for example, detection of grasping of the object by the gripper), and the like.

Note that the sensor unit 7 may not be provided, and only the image captured by the imaging unit 2 may be used to specify the object to be measured or to measure the feature amounts.

Furthermore, depending on the feature amounts, the imaging unit 2 may not be provided, and the detection information of the sensor unit 7 may be used to specify the object to be measured or to measure the feature amounts.

In addition, the operation of the user can also be recognized by the various sensors of the sensor unit 7 or can be recognized from an image captured by the imaging unit 2. For example, an operation using voice, an operation using body action (gesture), or the like can be detected, and in that case, there can be an example without the operation unit 6 as a key or other physical controllers, as a touch panel, or the like.

The display unit 9 is a display unit that performs various types of display for the user (such as a photographer), and for example, the display unit 9 includes a display device, such as an LCD (Liquid Crystal Display) and an organic EL (Electro-Luminescence) display, mounted on the measurement apparatus 1.

The display control unit 8 executes a process for causing the display unit 9 to execute a display operation. For example, the display control unit 8 includes a character generator, a display driver, and the like and causes the display unit 9 to execute various types of display on the basis of the control of the control unit 5.

In addition, the display control unit 8 may also cause the display unit 9 to display the image captured by the imaging unit 2 as a monitoring image (so-called image through the lens) or may cause the display unit 9 to reproduce and display still images or moving images recorded in a recording medium.

In addition, the display control unit 8 may also cause the display unit 9 to display various operation menus, icons, messages, and the like, that is, a GUI (Graphical User Interface), on the screen on the basis of an instruction of the control unit 5.

The display unit 9 may be included in the measurement apparatus 1. Alternatively, a separate display device may be used, and the display device may function as the display unit 9.

The storage unit 10 includes, for example, a non-volatile memory and stores, for example, image files of still image data, moving image data, and the like captured by the imaging unit 2, attribute information of the image files, thumbnail images, and the like. In addition, the storage unit 10 is also used as an area for storing information of measurement results, various types of accompanying information corresponding to the measurement, and various types of detection information obtained by the sensor unit 7 in the measurement. In addition, the storage unit 10 is also used as an area for storing setting information, such as a target value of work.

There can actually be various modes of the storage unit 10. For example, the storage unit 10 may be a flash memory built in the measurement apparatus 1 or may be in a mode including a memory card (for example, portable flash memory) that can be attached to and detached from the measurement apparatus 1 and a card recording and reproduction unit for recording, reproducing, and accessing the memory card. In addition, an example of the mode in which the storage unit 10 is built in the measurement apparatus 1 includes a mode in which the storage unit 10 is realized as an HDD (Hard Disk Drive) or the like.

Figure 2:
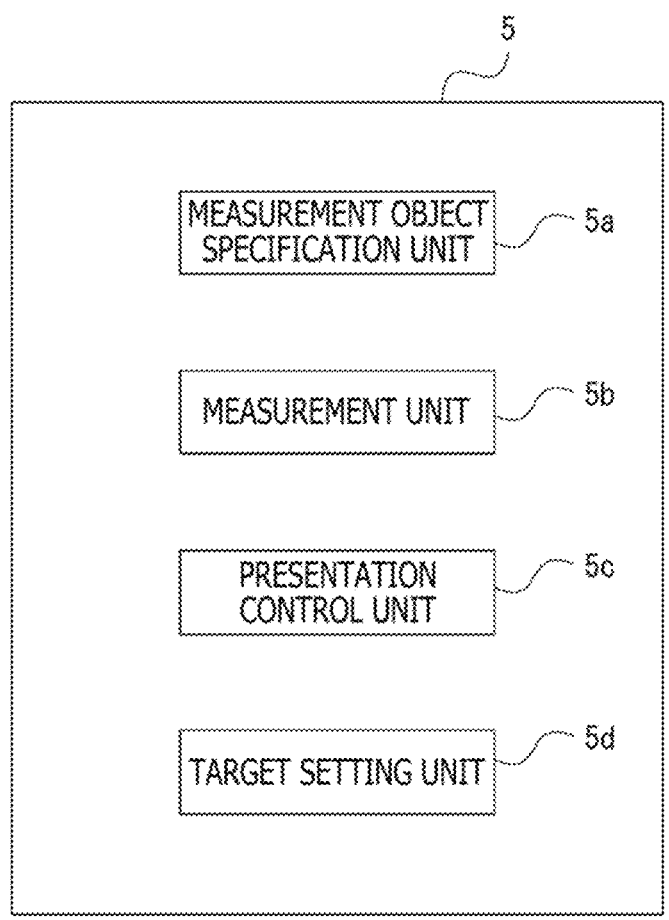
FIG. 2 is an explanatory diagram of a functional configuration of the measurement apparatus in the embodiments.

The configuration as described above is provided in the case of the present embodiments, and in addition, a software program provides the control unit 5 with a functional configuration illustrated in FIG. 2.

That is, the control unit 5 includes functions of a measurement object specification unit 5a, a measurement unit 5b, a presentation control unit 5c, and a target setting unit 5d.

Note that, although the control unit 5 includes the functions in FIG. 2, part or all of the measurement object specification unit 5a, the measurement unit 5b, the presentation control unit 5c, and the target setting unit 5d may be included in, for example, the image analysis unit 4. The performance, the throughput, necessary functions, and the like in the microcomputer, the processor, and the like mounted on the measurement apparatus 1 actually depend on design situations and the like of individual apparatuses, and for example, there can be various specific implementation modes of the arithmetic processing apparatus including functions, such as the image signal processing unit 3, the image analysis unit 4, the control unit 5, and the display control unit 8 in FIG. 1. For example, the functions may be provided by one microcomputer, or the functions may be appropriately allocated and mounted on two microcomputers.

Therefore, the functional configuration illustrated in FIG. 2 may not be provided in the control unit 5, and it is only necessary that the functional configuration be provided in at least the measurement apparatus 1.

The measurement object specification unit 5a executes a process of specifying the object to be measured on the basis of the detection of grasping of the object by the gripper. The process of specifying the object to be measured is, for example, a process of the control unit 5 instructing the image analysis unit 4 to set the condition of the object to be measured (grasping by the gripper) to cause the image analysis unit 4 to specify the pixel range of the object to be measured, a process of actually specifying the pixel range of the object to be measured, or the like.

The gripper is, for example, a thing that can grasp the object, such as the hands or fingers of the worker, the hands or fingers of the worker wearing gloves or a predetermined tool, a tool that can grasp the object through operation by a person, a tool that can automatically grasp the object, and a robot arm.

The object denotes various objects, such as crops like grapes, bananas, or tomatoes, natural objects like trees or animals, and industrial products, and the object to be measured is all or part of the objects specified by grasping.

The measurement object specification unit 5a can use the image analysis result of the image analysis unit 4 or the detection result of the sensor unit 7 to recognize the actual grasping of the object by the gripper. For example, in a case where a specific event such as "the hand holds the branch of a bunch of grapes" is obtained as an image analysis result of the image analysis unit 4, the measurement object specification unit 5a recognizes that "the gripper grasps the object." Alternatively, when the state in which the hand is near the branch of a bunch of grapes is determined in the analysis result of the image analysis unit 4, and the pressure sensor of the sensor unit 7 (pressure sensor mounted on the finger of the worker) detects a pressure equal to or higher than a predetermined pressure, the measurement object specification unit 5a recognizes an occurrence of a specific event such as "the hand holds the branch of a bunch of grapes" and determines that "the gripper holds the object."

As in these examples, the measurement object specification unit 5a recognizes that "the gripper grasps the object" on the basis of the determination process of the image analysis unit 4 or the detection information of some sensors as the sensor unit 7.

The measurement unit 5b executes a process of acquiring the measurement result of the feature amount of the object to be measured specified by the measurement object specification unit 5a. For example, the measurement unit 5b executes a process necessary for acquiring the measurement result of the number of pieces in the bunch of grapes as the object to be measured.

The counting process as actual measurement may be executed based on the image analysis by the image analysis unit 4, and the measurement unit 5b may acquire the measurement result. Alternatively, the measurement unit 5b may count the number of image areas recognized as pieces of grapes by the image analysis unit 4. Furthermore, depending on the feature amount to be measured, the measurement unit 5b may acquire the quantity as detection information of the sensor unit 7 or may perform counting based on the detection information to calculate the measurement result. That is, it is only necessary that the measurement unit 5b (control unit 5) acquire at least the measurement result in the measurement process, regardless of whether or not the measurement unit 5b executes the measurement.

Therefore, the measurement unit of the present disclosure may denote the measurement unit 5b of the embodiments in terms of acquiring at least the measurement result. The measurement unit may also be configured to execute the measurement process and may be perceived as a concept including the measurement unit 5b and the image analysis unit 4, a concept including the measurement unit 5b and the sensor unit 7, or a concept including the measurement unit 5b, the image analysis unit 4, and the sensor unit 7.

Note that the feature amount to be acquired as a measurement result by the measurement unit 5b is not limited to the quantity, such as the number of pieces of grapes, and the feature amount can also be a value that can be quantified or that can be compared and evaluated, such as the dimension (size) of the object to be measured, the color, the component content, the component ratio, the sugar content, the moisture content, and the estimated price.

The presentation control unit 5c executes a process for presentation based on the measurement result as a result of the measurement process obtained by the measurement unit 5b.

Specifically, the process is, for example, a process of controlling the display control unit 8 to cause the display unit 9 to display the information of the number of pieces in the bunch of grapes. Alternatively, the presentation control unit 5c may present information determined from the measurement result, such as determination information of "proper," "improper," "appropriate quantity," "insufficient," and "excessive," or guide contents for subsequent work, instead of the numerical value of the measurement result.

Note that, although the measurement result is presented by display in the examples described in the embodiments, the numerical value as a measurement result for the user or the presentation based on the measurement result may be provided by sound or by vibration. Therefore, although not illustrated in FIG. 1, a sound output unit, a vibration unit, and the like may also be provided.

For example, a sound message, such as "the measurement result is 38 pieces" and "the quantity is appropriate," may be output, or "proper" and "improper" may be presented in difference vibration patterns.

The target setting unit 5d executes a process of setting the target value of the feature amount measured according to, for example, the input or the selection by the user. For example, in a case where the user as a grape farmer intends to set the number of pieces in a bunch of grapes to 35, the user inputs a target value of "35," and the target setting unit 5d sets the target value to "35" and executes a process of storing the target value in, for example, the storage unit 10. In the measurement process, a comparison process of the current measurement value and the stored target value is executed to perform presentation appropriate for the user.

The target setting unit 5d is a function provided in the case of executing a process of a fifth embodiment.

Furthermore, in a case where the function of the target setting unit 5d is provided, the presentation control unit 5c also performs presentation based on the result of the comparison process of the current measurement value and the stored target value.

Although the control unit 5 has the functional configuration described above, there is also a case in which, for example, the control unit 5 and the image analysis unit 4 are provided by one microcomputer, processor, or the like. In that case, the functional configuration of FIG. 2 can be adopted in the microcomputer or the like.

The measurement apparatus 1 of the embodiments has the configuration as illustrated in FIGS. 1 and 2, and a specific mode of using the measurement apparatus 1 with the configuration to measure the number of pieces of grapes will be described.

With the decline in the number of farmers and the aging of farmers, efficient management of agriculture with high profitability by young farmers is anticipated.

Particularly, one of the operations that require improved efficiency in the production of raw grapes is an operation called "berry thinning."

When general raw grapes grow in a natural state, one bunch includes 50 to 70 pieces. If the grapes are grown with this number of pieces, the grapes will have small pieces with low sugar content, and the commercial value will be low. Therefore, the grapes need to be thinned out to an appropriate number of pieces, and this work is called "berry thinning."

In addition, the pieces of grapes gradually grow after withering of flowers, and after several weeks, adjacent pieces are rubbed against each other. Therefore, the berry thinning work of all of the bunches in the farm needs to be completed in this short time. Furthermore, the berry thinning work is work that needs to be performed in a significantly short period, and the efficiency is important. Specifically, the berry thinning needs to be performed for all bunches of grapes in the farm in a period of about two weeks, and the efficiency is highly demanded.

Important points in the berry thinning include the following.

Remove the pieces with a poor shape.
Make the density of pieces uniform.
Make the number of pieces appropriate.

Among these, the most difficult one to make it efficient is to make the number of pieces appropriate.

Note that the appropriate value of the number of pieces varies depending on the type. For example, the appropriate value is 30 to 35 pieces for a variety A, 40 to 45 pieces for a variety B, 50 pieces for a variety C, and so forth. In addition, the appropriate value also varies depending on the commercial value of the grapes to be produced, and high-priced delicious grapes with large pieces are basically obtained by reducing the number of pieces.

As described above, the berry thinning work needs to be carried out in a significantly short time, and the worker cannot count the number of pieces of each bunch every time.

According to a worker, the berry thinning work that has been performed by the farmers include the following.

1. In the early morning at the start of the work, the number of pieces of just one bunch is counted, and the berry thinning is performed to make the value appropriate.

2. The bunch is carefully observed to create an image of the berry thinning completion state in the mind.

3. The berry thinning work is continuously repeated to attain the image.

However, it is difficult to make the number of pieces appropriate due to factors such as physical conditions and time (the pieces are hard to see in the evening when the sun goes down).

Under the circumstances, a measurement apparatus that measures the number of pieces in a bunch of grapes is demanded.

In this case, there can be an application that counts and displays the number of pieces based on, for example, an image taken by a camera of a smartphone.

For example, the worker presses a shutter button of the smartphone to take a picture of the bunch. The application functioning in the smartphone analyzes the image to measure and display the number of pieces. This allows the worker to recognize the number of pieces.

However, the operation of using the smartphone to take a picture (for example, action of pressing the imaging button on the screen) during the berry thinning work is an operation not fit into the berry thinning work, and the operation imposes a load on the worker. In this regard, it is difficult to make the berry thinning work efficient.

Furthermore, other bunches may appear in the captured image in addition to the bunch to be measured, not only in a case of the smartphone, but also in other cases of using a camera to take a picture to measure the number of pieces. Particularly, the bunches are dense in the farm. Therefore, the worker may need a skill of photographing in order to designate and measure only a specific bunch, or other bunches may appear in the image so that the counting becomes inaccurate.

Furthermore, in a case where a picture is taken in one direction in imaging, the number of pieces on the back side is uncertain based on the image. Therefore, for example, the number of pieces on the front side appearing in the image is multiplied by a coefficient to calculate the estimated number of all pieces. However, in this case, an error may be large depending on the coefficient, and there may be a problem in accuracy.

In view of the circumstances, the object to be measured is clearly specified first to thereby increase the accuracy of measurement in the present embodiments.

Furthermore, the measurement is performed at appropriate timing to obtain the measurement result, and the burden on the worker in the operation is prevented in the measurement.

Figure 3:
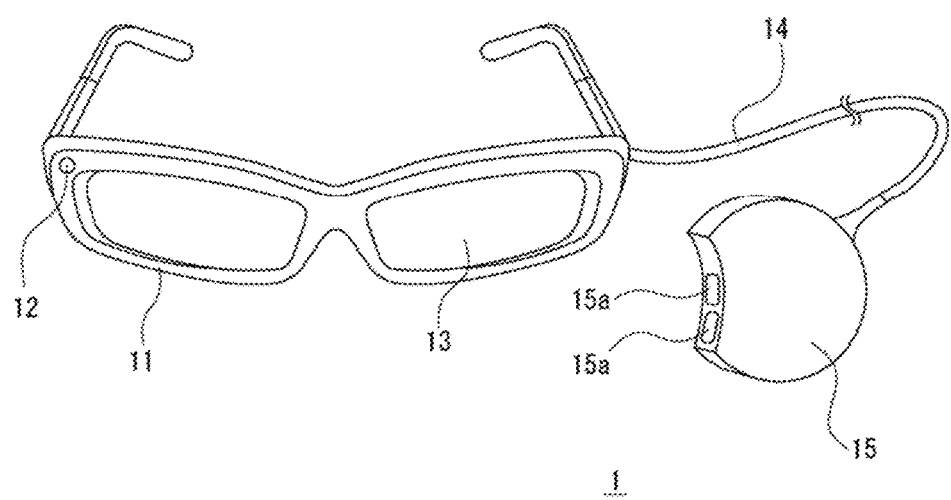
FIG. 3 is an explanatory diagram of an example of a mode of the measurement apparatus in the embodiments.

An example of a mode of the measurement apparatus 1 suitable for the concept includes a mode including a glass unit 11 as illustrated in FIG. 3.

In the example of FIG. 3, the measurement apparatus 1 includes the glass unit 11 and a control unit 15 connected by a cord 14.

Figure 4:
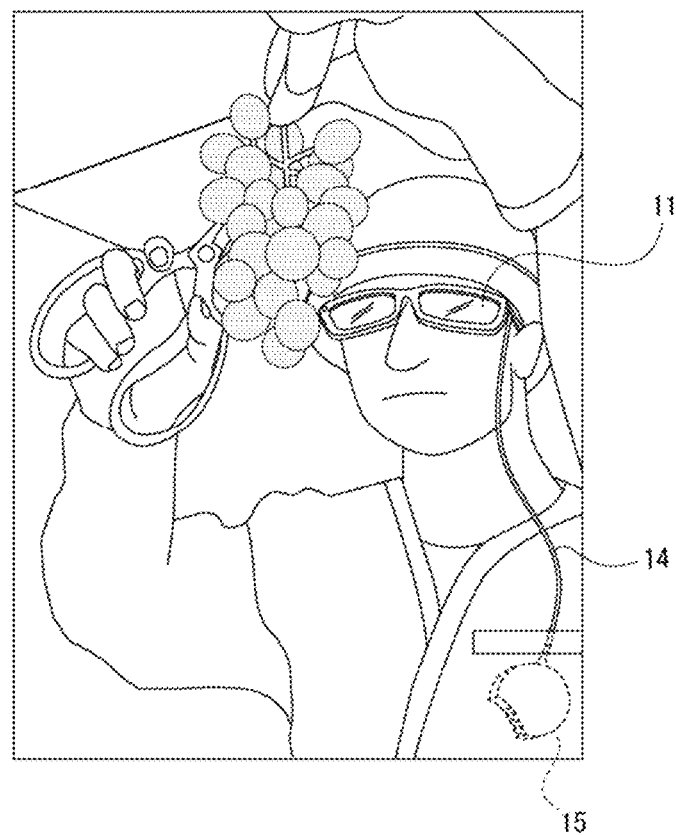
FIG. 4 is an explanatory diagram of a use state of the measurement apparatus in the embodiments.

The glass unit 11 is an eyeglass type, and the worker can wear the glass unit 11 like sunglasses during the berry thinning work as illustrated in FIG. 4.

The control unit 15 includes a small housing, and the worker stores the control unit 15 in a pocket of clothes or the like.

A camera 12 is mounted on the glass unit 11 to allow the worker to take a picture in front of the worker.

In addition, the front surface of the eyeglass-type glass unit 11 includes an on-glass display unit 13. The on-glass display unit 13 is usually, for example, a transparent or semi-transparent liquid crystal panel or the like. Although the user can see the on-glass display unit 13 as just a glass and can check forward, necessary display can be performed on the glass.

Figure 5:
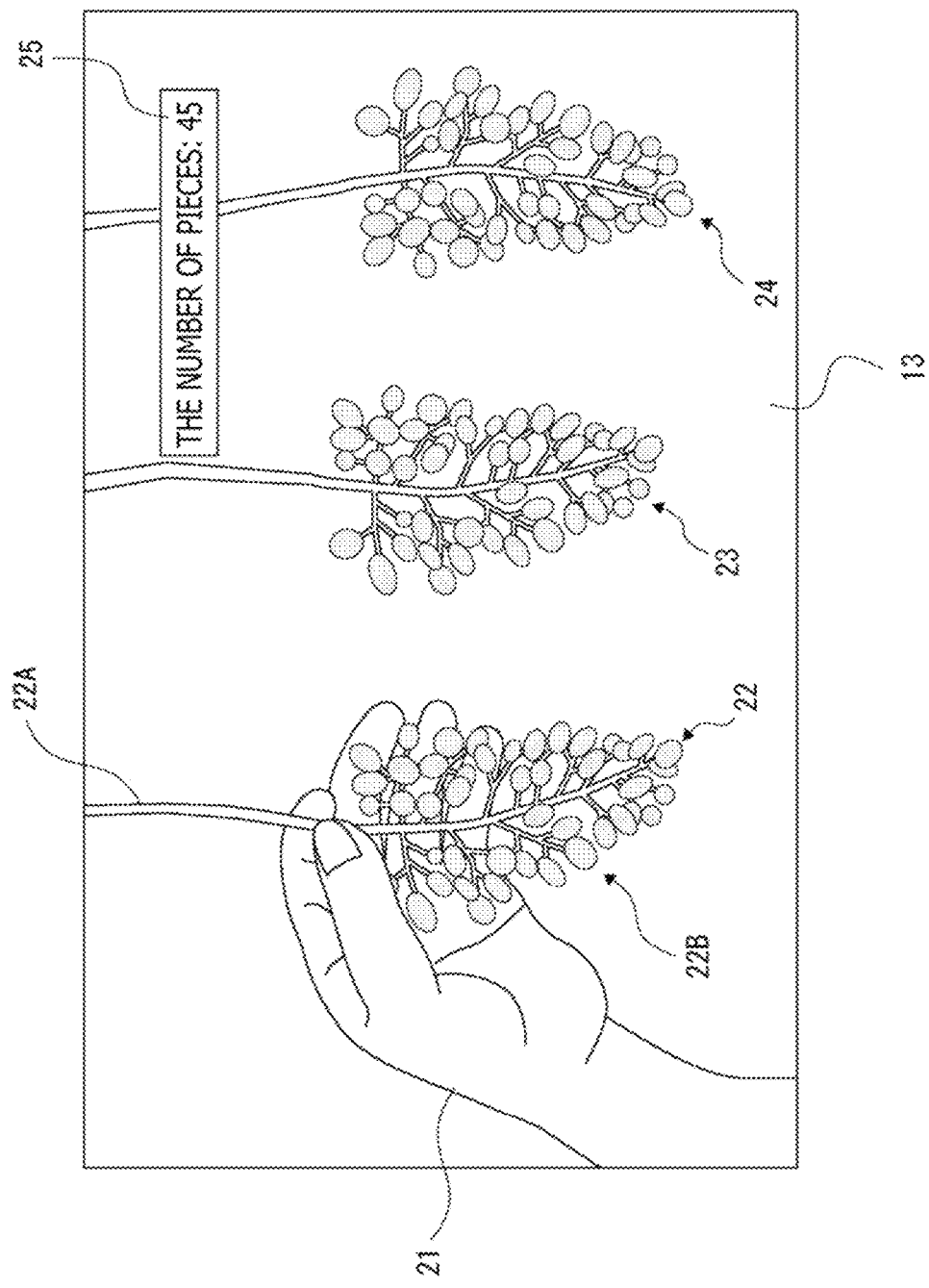
FIG. 5 is an explanatory diagram of a display state in the embodiments.

For example, FIG. 5 illustrates a state of display on the on-glass display unit 13 while the user is wearing the glass unit 11 as in FIG. 4.

The user can see grapes 22, 23, and 24 through the transparent plate as the on-glass display unit 13, and in this state, for example, number-of-pieces display 25, such as "the number of pieces 45," illustrated in FIG. 5 is performed. This allows the user to check the number of pieces measured.

Note that the on-glass display unit 13 may display the captured image of the camera 12 as an image through the lens, instead of being transparent or semi-transparent.

An operation button 15a is provided on the control unit 15, and for example, a power on/off operation and the like can be performed.

Note that the camera 12, the on-glass display unit 13, and the operation button 15a are modes of the imaging unit 2, the display unit 9, and the operation unit 6 in FIG. 1, respectively.

The glass unit 11 and the control unit 15 provided with, for example, the components of the configuration in FIG. 1 function as the measurement apparatus 1.

In the example described above, the camera 12 as the imaging unit 2 and the on-glass display unit 13 as an example of the display unit 9 are mounted on the glass unit 11, and the operation button 15a as an example of the operation unit 6 is mounted on the control unit 15 in the example. However, the components illustrated in FIG. 1 may be mounted on either one of the glass unit 11 and the control unit 15.

In addition, there can also be a mode in which all of the components in FIG. 1 are arranged in the glass unit 11, and the control unit 15 is not provided.

Note that the mode of the measurement apparatus 1 is not limited to the mode based on the glass unit 11 and the control unit 15 of FIG. 3, and other modes will be described later. Hereinafter, an example of the mode of FIG. 3 will be described.

2. Processing Example of First Embodiment

Figure 6:
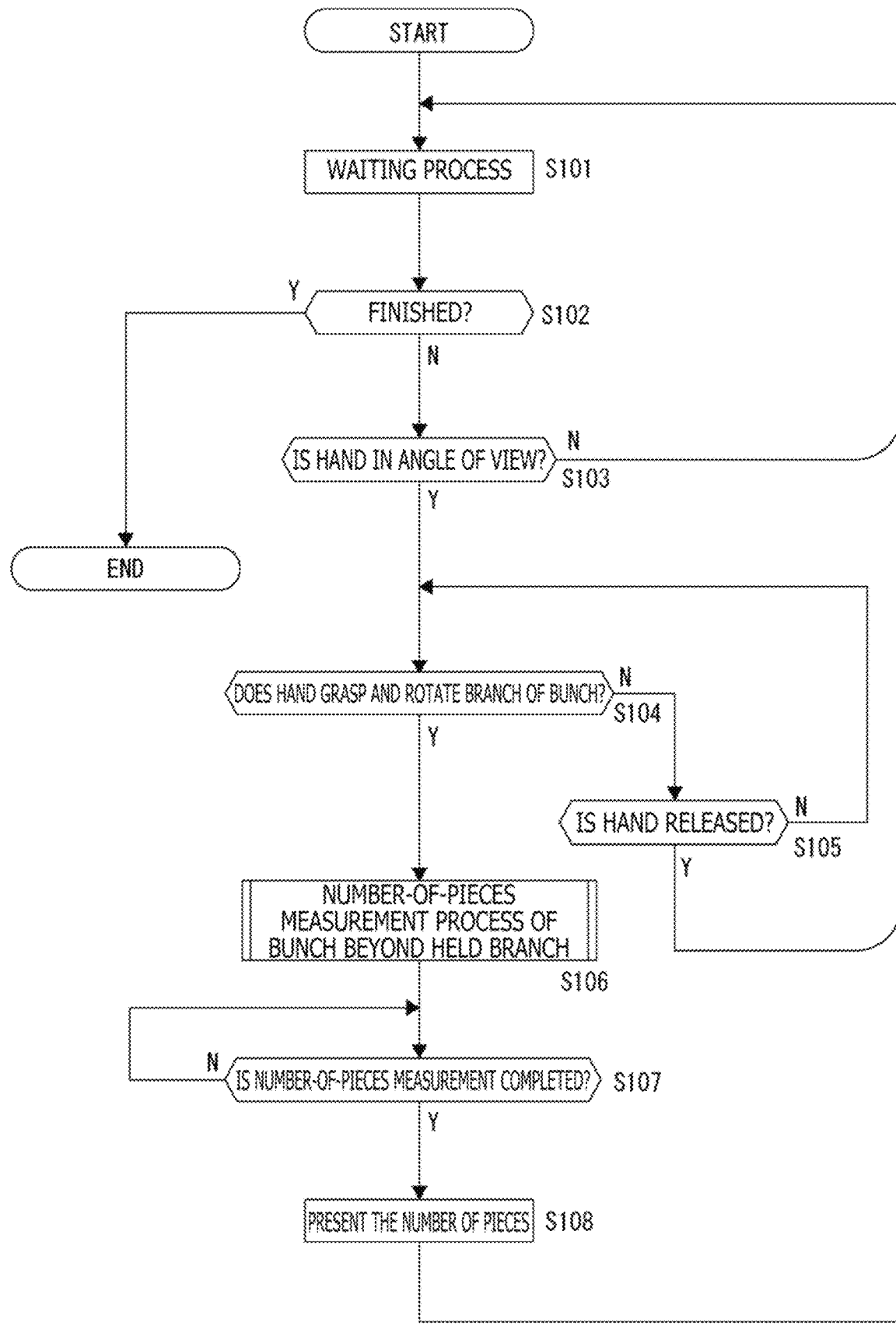
FIG. 6 is a flow chart of a processing example of a first embodiment.

A processing example as a first embodiment suitable for using the measurement apparatus 1 in the berry thinning work of grapes will be described in FIG. 6. FIG. 6 is a processing example executed by the control unit 5 using the functions of the measurement object specification unit 5a, the measurement unit 5b, and the presentation control unit 5c of FIG. 2.

The control unit 5 of the measurement apparatus 1 executes the process of FIG. 6 in the power-on state.

In step S101, the control unit 5 executes a waiting process.

The waiting process is a process of using the imaging unit 2 to capture an image and monitoring the analysis result of the captured image of the image analysis unit 4, the detection result of the sensor unit 7, and the operation of the operation unit 6.

More specifically, the control unit 5 monitors whether or not an operation indicating the end of the measurement of the operation unit 6 is performed. The operation indicating the end of the measurement is, for example, an operation for stopping the measurement to perform various types of settings, an operation for a transition to another mode, a power off operation, or the like. In a case where the control unit 5 detects the operation, the control unit 5 ends the process of FIG. 6 from step S102 and shifts to another necessary process.

In the waiting process, the control unit 5 also detects whether or not the hand of the worker is in the angle of view of the imaging unit 2. The fact that the hand is in the angle of view indicates a state in which the hand of the worker is in the image captured by the imaging unit 2.

Examples of the method of discriminating the hand include the following.

Determining the existence of the hand in the angle of view by discriminating the skin color based on image analysis.

Discriminating the hand of a person based on the temperature by using an image captured by a thermo tracer.

Discriminating the hand by using a method of discriminating the hand of a person realized by machine learning or deep learning by using an image captured by an image sensor.

Discriminating the hand by using a method of discriminating the hand of a person realized by machine learning or deep learning by using an image captured by a TOF sensor or a stereo camera.

Discriminating the hand by using a method of discriminating gloves in specific color and pattern worn by the worker.

Figure 7:
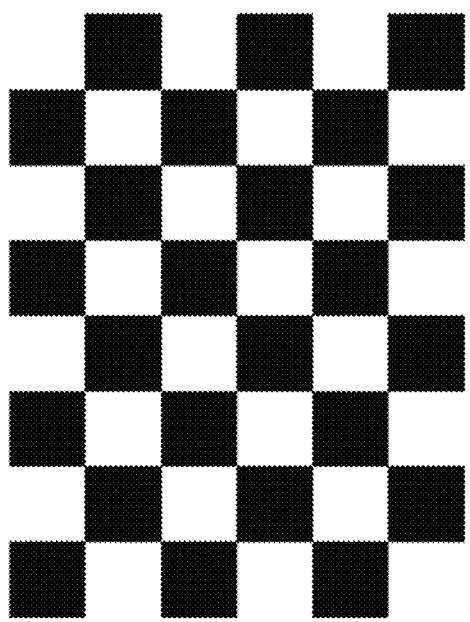
FIG. 7 is an explanatory diagram of an example of a discrimination pattern that can be used in the embodiments.

The method of discriminating the gloves worn by the worker can be, for example, a process in which the worker wears gloves in a checkered pattern as illustrated in FIG. 7, and the pattern is discriminated by image recognition. In addition, the color of the gloves may be a color (for example, purple) that does not exist in the farm, and whether the hand is in the angle of view may be discriminated based on color determination in the image.

Once the control unit 5 detects that the hand is in the angle of view of the imaging unit 2, that is, in the captured image, the control unit 5 monitors the timing of the execution of measurement. That is, the control unit 5 in step S104 monitors whether the hand grasps the branch of the bunch of grapes and further rotates the bunch in the grasped state.

Examples of means for discriminating whether the hand grasps the branch include the following.

Installing a pressure sensor on a fingertip or a glove of the worker to discriminate whether the hand grasps the branch based on the change in pressure.

Using a thermo tracer to perceive the change in temperature based on the change in the blood flow of the fingers. That is, the change in the blood flow after grasping the branch is used for the detection.

Using the captured image for the discrimination. For example, a discrimination algorithm of the state of the hand grasping the branch realized by machine learning is used for the discrimination.

In addition, an example of the method of discriminating the operation of rotating the bunch includes applying an analysis process to the captured images to recognize the pieces of grapes and determining the rotation of the bunch based on the movement of the positions of the pieces in accordance with the advance of the frames of the captured images.

The control unit 5 returns from step S105 to S101 in a case where the control unit 5 detects that the hand of the worker with the hand in the captured image is released without rotating the branch of the bunch of grapes or in a case where the hand further exits from the angle of view even if the hand once grasps the branch of the bunch of grapes.

When the control unit 5 detects that the hand in the angle of view holds and rotates the branch of the bunch, the control unit 5 is triggered by this to automatically start to measure the number of pieces. That is, the control unit 5 proceeds from step S104 to S106 and executes a number-of-pieces measurement process of the bunch beyond the held branch.

In the measurement of the number of pieces, the control unit 5 acquires captured images of the bunch in a plurality of directions upon the rotation of the bunch and measures the number of three-dimensionally existing pieces including the number of pieces existing on the back side of the bunch.

Figure 8:
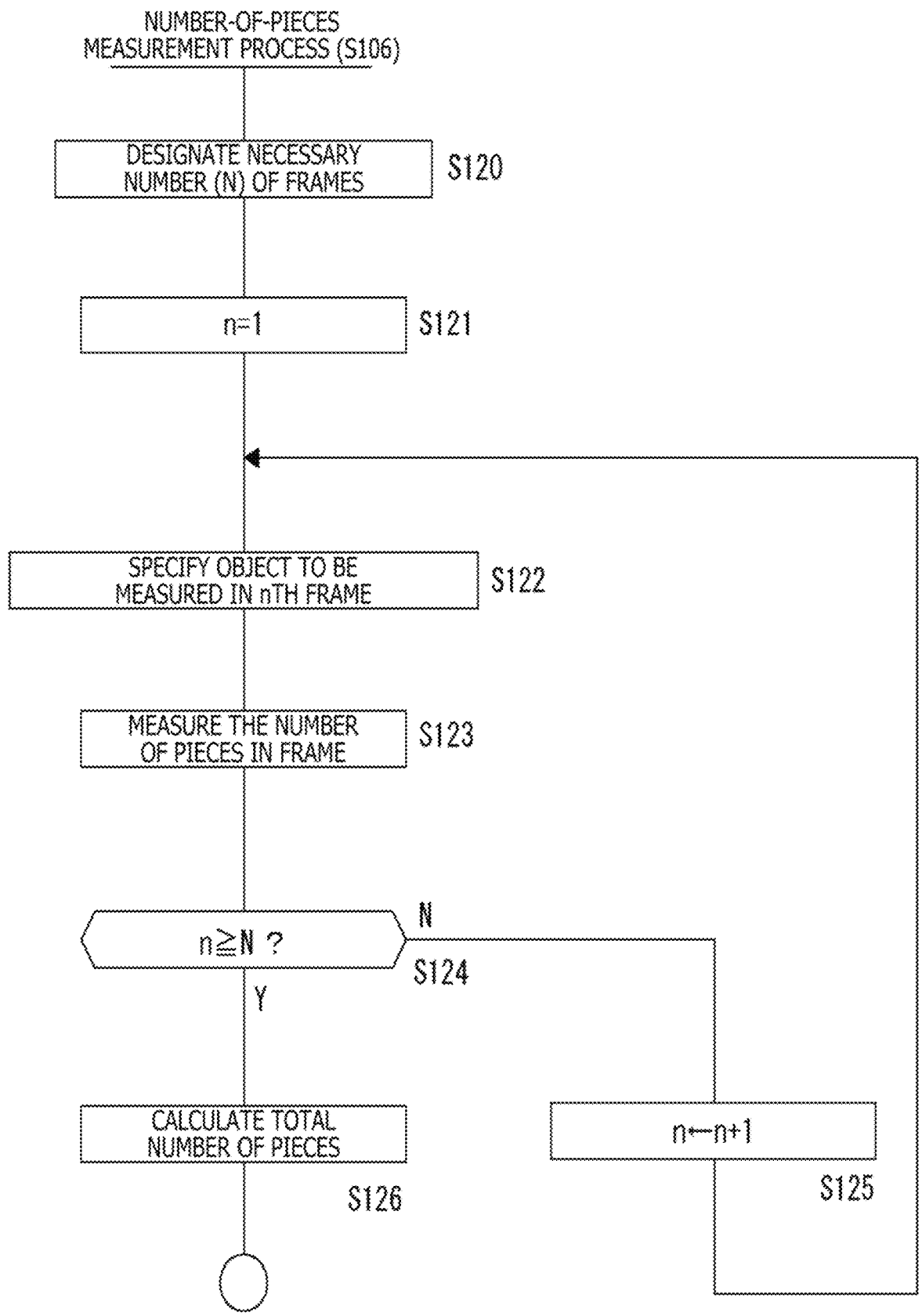
FIG. 8 is a flow chart of a measurement process in the embodiments.

The number-of-pieces measurement process of step S106 is illustrated in detail in FIG. 8.

In step S120 of FIG. 8, the control unit 5 designates a necessary number (N) of frames of the captured images. For example, the control unit 5 sets, as frames to be used for the measurement, a required number of frames in a period in which the worker holds and rotates the branch of the bunch.

Note that the worker can rotate the bunch of grapes approximately 120 degrees to 150 degrees to observe the number of pieces of grapes. This is because the branch is usually not cut even when the branch is rotated by an angle of that level.

Furthermore, the pieces on the back side at first generally appear in the frame images after the rotation of approximately 120 degrees to 150 degrees. Therefore, a plurality of frames in the period in which the worker rotates the bunch of grapes approximately 120 degrees to 150 degrees are extracted to measure the number of pieces from the frames.

Here, it is assumed that the speed of the worker rotating the bunch of grapes is 360 degrees per second. In a case of the speed of this level, it is appropriate to capture images at a frame rate of, for example, approximately 120 fps. The control unit 5 designates a required number (N) of pieces of frame image data as a processing target in the frames of the captured images obtained at the frame rate.

Depending on the frame rate and the rotation speed, the N frames may be continuous frames or may be frames extracted intermittently. This may be variable according to the actual rotation period.

The control unit 5 sets n=1 for a variable n in step S121 and proceeds to step S122. In step S122, the control unit 5 specifies the object to be measured in an nth frame among the designated frames. The variable is n=1 first, and the control unit 5 executes a process of specifying the object to be measured in a first frame of the N frames designated as the processing target. For example, the control unit 5 instructs the image analysis unit 4 to specify, as the object to be measured, the bunch of grapes in which the branch is held by the hand of the worker.

That is, the bunch of grapes, in which the branch is held by the hand of the worker, recognized by the image analysis unit 4 is specified as the object to be measured. Specifically, the image analysis unit 4 determines the area (pixel area) of the bunch positioned below the hand of the worker in the image based on image analysis, luminance edge detection, color determination, or the like. In this way, the image analysis unit 4 specifies the pixel range of the bunch of grapes as the object to be measured in the image of the frame as the processing target.

In step S123, the control unit 5 (or the image analysis unit 4) measures the number of pieces of grapes in the frame, and the control unit 5 obtains a measurement result.

That is, the control unit 5 determines the image of the pieces in the pixel range specified as the object to be measured and measures the number of pieces.

Once the control unit 5 measures the number of pieces in one frame, the control unit 5 checks whether or not the variable n reaches the designated number N of frames in step S124. If the variable n does not reach the number N of frames, the control unit 5 increments the variable n in step S125 and returns to step S122.

Therefore, the specification of the pixel range as the object to be measured in the image and the measurement of the number of pieces in the pixel range are sequentially performed in the N frames selected as the processing target.

Note that the process targets the images of a plurality of frames captured in the period in which the bunch of grapes is rotated by the worker.

In this case, the rotation angle of the bunch is figured out from the amount of movement of the pieces in the image, and the pieces are not counted again when the pieces measured first are moved to other places after the rotation. In this way, the number of pieces can be accurately figured out.

Furthermore, in a case where, for example, the pieces counted in the first frame appear in a frame after one round based on the rotation angle from the first frame counted first, the pieces are not counted in order to perform accurate counting of the number of pieces.

In this way, the pieces of grapes that cannot be viewed in one direction (one frame) can be accurately recognized, and the pieces of grapes can be measured without double counting.

In addition, examples of the method of measuring the pieces of bunch beyond the grasped branch include the following:

Using the TOF to measure the position of the hand and measuring the number of pieces at the same depth as the hand.

Using the stereo camera or the method of defocus to measure the depth to thereby recognize each piece to measure the number of pieces.

Using a plurality of IR (infrared) rays at a wavelength absorbed by water and at a wavelength not absorbed by water to detect and count the pieces. Note that other than the IR, visible light or other wavelengths may be used. The pieces of grapes contain more water than the branch, and due to the difference in moisture content, the peak corresponding to the pieces is formed at only a specific wavelength of the infrared light. Therefore, the part of the pieces with a large amount of moisture can be detected, and as a result, the number of pieces can be counted.

In the process of FIG. 8, the variable n reaches the designated number N of frames in step S124 at the end of the measurement of the number of pieces for each frame, and the process of the control unit 5 proceeds to step S126. The control unit 5 in step S126 adds the numbers of pieces counted in the frames to calculate the number of pieces of the entire bunch. That is, the control unit 5 obtains the measurement result of the number of pieces in the specific bunch of grapes as the object to be measured specified by the worker holding the bunch.

Once the measurement of the number of pieces is completed after the execution of the process of FIG. 8 in step S106 of FIG. 6, the control unit 5 proceeds from step S107 to step S108 and presents the number of pieces. For example, the control unit 5 instructs the display control unit 8 to cause the display unit 9 (for example, the on-glass display unit 13) to execute the number-of-pieces display 25 as illustrated in FIG. 5.

In this case, the control unit 5 may generate and display not only the number of pieces, but also a predetermined determination result or the like obtained from the measurement.

In addition, the measurement result may be presented not only by the display, but also by sound, vibration, or the like.

Once the process for the presentation is executed, the control unit 5 returns to the waiting process of step S101.

According to the process, the measurement object is specified when the worker grasps the branch by hand, and the measurement is executed when the worker rotates the bunch.

The object to be measured is specified on the basis of the grasped branch. Therefore, even if, for example, a plurality of grapes 22, 23, and 24 exist in the angle of view as illustrated in FIG. 5, only a bunch 22B of grapes 22 below a held branch 22A is specified as the object to be measured. As a result, although the grapes appear in the angle of view, each set of grapes can be accurately measured.

In addition, for example, an extra operation, such as pressing the shutter button for imaging, is not necessary, and the berry thinning work is not obstructed.

In addition, the image information of a plurality of frames and the information of the rotation angle of the bunch can be used to prevent the remeasurement of the pieces measured first, and therefore, the number of pieces can be accurately measured.

3. Processing Example of Second Embodiment

Figure 9:
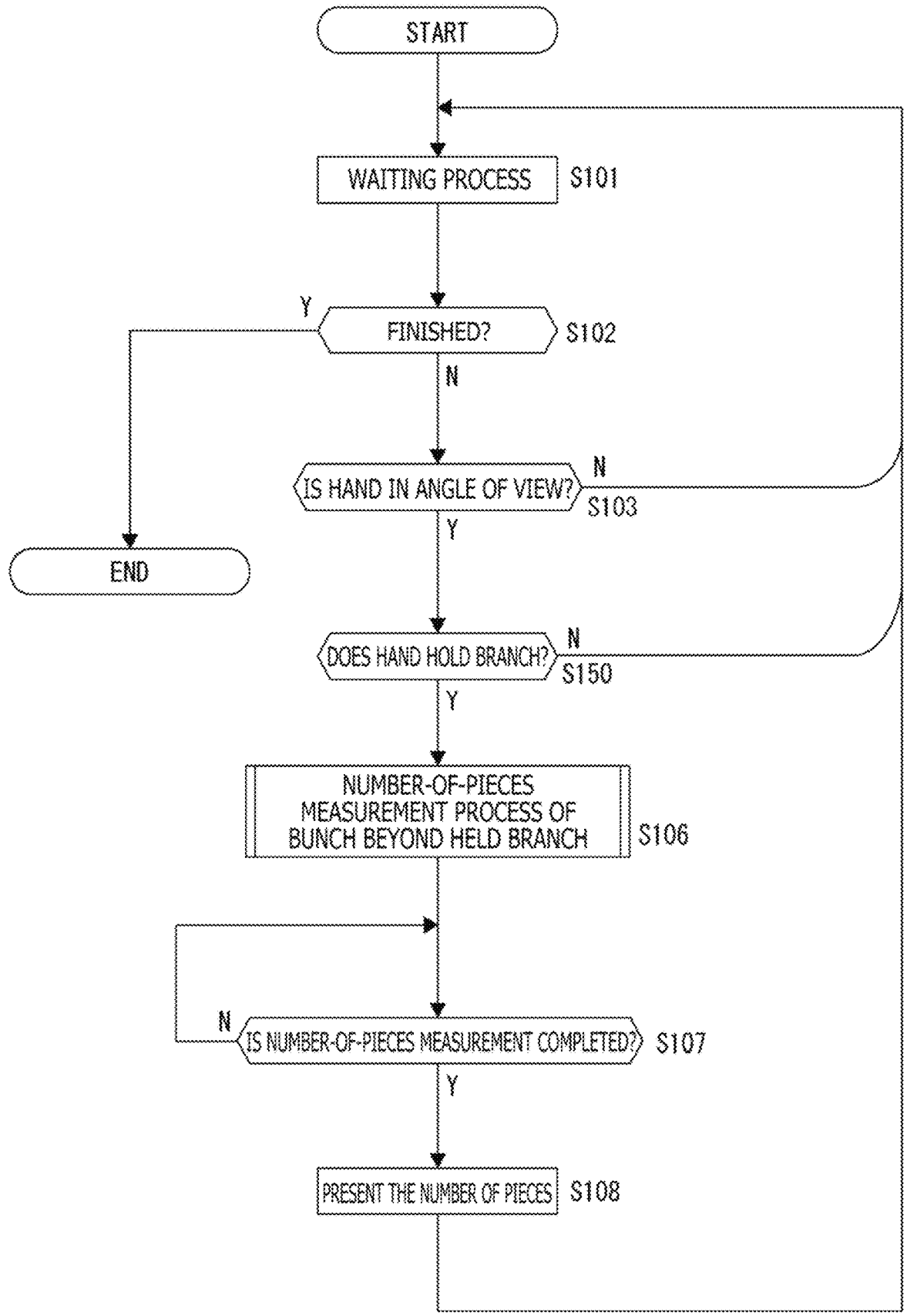
FIG. 9 is a flow chart of a processing example in a second embodiment.

A processing example of a second embodiment will be described with reference to FIG. 9. FIG. 9 is a processing example executed by the control unit 5 using the functions of the measurement object specification unit 5a, the measurement unit 5b, and the presentation control unit 5c of FIG. 2. Note that the same step numbers are provided to the same processes as the processes already described, and the description will not be repeated.

The control unit 5 executes the waiting process in step S101 and monitors for the end of the process in step S102. The control unit 5 monitors whether or not the hand of the worker enters the angle of view in step S103.

In the example, once the control unit 5 detects that the hand enters the angle of view, the control unit 5 proceeds to step S150 and determines whether or not the hand holds the branch.

When the hand appearing in the angle of view does not hold the branch, the control unit 5 returns to step S101. When the control unit 5 detects that the hand holds (grasps) the branch, the control unit 5 regards the detection as a trigger for the start of the measurement and proceeds to step S106 to start the number-of-pieces measurement process. The process is executed as in, for example, FIG. 8. In this case, the worker can rotate the bunch of grapes to accurately measure the number of pieces from the images of a plurality of frames.

Once the number-of-pieces measurement process is completed, the control unit 5 proceeds from step S107 to S108 and controls the presentation of the number of pieces or the like as a measurement result.

In this way, the process of FIG. 9 is an example of starting the measurement by discriminating the fact that the hand holds the branch.

Note that, although the fact that the hand holds the branch is detected to start the measurement in the example, the worker may not rotate the bunch. Therefore, in a case where the rotation of the bunch is not detected for equal to or more than a predetermined time, the measurement can be finished with an error.

Alternatively, the measurement may be performed regardless of whether the bunch is rotated. For example, in a case where the rotation is detected, the images of a plurality of frames of the bunch of grapes viewed in different directions are used to measure the number of pieces in the process of FIG. 8. On the other hand, in a case where the bunch is not rotated, the images of the frames are substantially the same images. Therefore, the number of pieces of grapes is measured from the image of one frame (image viewed in one direction), and the number of pieces is multiplied by a coefficient as in a fourth embodiment described later to obtain an estimated value of the number of pieces on the back side (not appearing in the image). The number of pieces of the entire bunch is calculated from the estimated value.

In addition, there may be an object or a feature amount that can be accurately measured regardless of whether or not the object to be measured is rotated. In such a case, the measurement can be started upon the grasp of the object, and for example, an image in one direction or sensing information can be used to appropriately specify the object to be measured to measure the feature amount.

4. Processing Example of Third Embodiment

Figure 10:
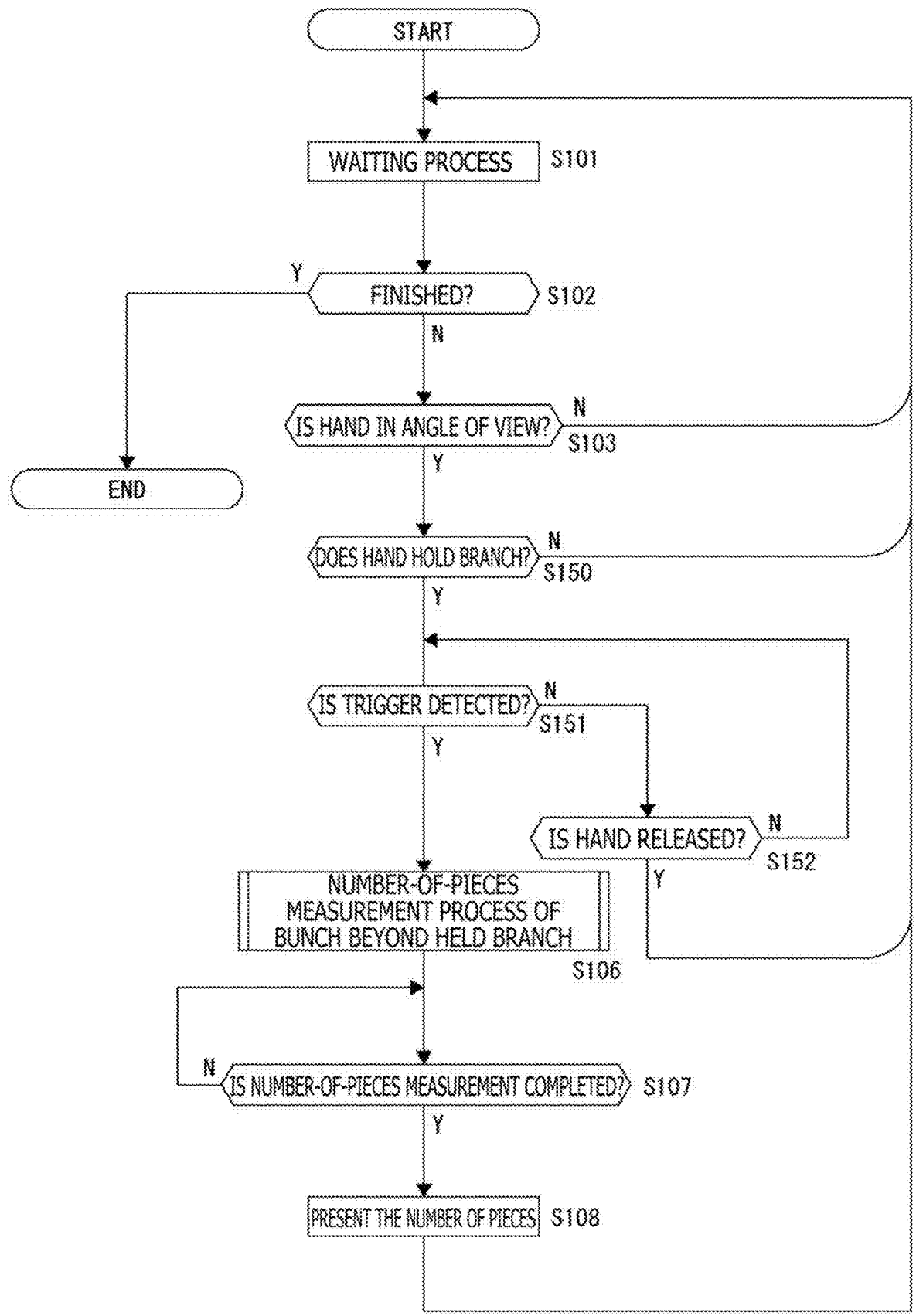
FIG. 10 is a flow chart of a processing example in a third embodiment.

A processing example of a third embodiment will be described with reference to FIG. 10. The process of FIG. 10 is also a processing example executed by the control unit 5 using the functions of the measurement object specification unit 5a, the measurement unit 5b, and the presentation control unit 5c of FIG. 2, and the difference from FIG. 9 is that processes of steps S151 and S152 are executed while the hand holding the branch is detected in step S150.

In a case where the control unit 5 determines that the hand holds the branch in step S150, the control unit 5 does not immediately determine to start the measurement. The control unit 5 monitors whether or not a trigger for starting the measurement is detected in step S151 and monitors whether or not the hand is released in step S152.

The control unit 5 detects the trigger for starting the measurement based on the determination result from the image of the image analysis unit 4 or the detection information of the sensor unit 7.

In a case where the control unit 5 detects that the hand of the worker is released without detecting the trigger even if the hand once grasps the branch of the bunch of grapes, or in a case where the control unit 5 detects that the hand of the worker further exits from the angle of view, the control unit 5 returns from step S152 to S101.

Furthermore, in a case where the control unit 5 detects a predetermined trigger in the state in which the hand of the worker holds the branch of the bunch, the control unit 5 proceeds from step S151 to S106 and starts the number-of-pieces measurement process. The process is executed as in, for example, FIG. 8. In this case, the worker can rotate the bunch of grapes to accurately measure the number of pieces from the images of a plurality of frames.

Once the number-of-pieces measurement process is completed, the control unit 5 proceeds from step S107 to S108 and controls the presentation of the number of pieces or the like as a measurement result.

As described above, in the example, a predetermined action as a trigger is detected to start the measurement of the feature amount of the object to be measured in the state in which the worker grasps the branch by hand. The predetermined action as a trigger can be an audio action, such as a speech of the worker and generation of a predetermined sound, a gesture action by the hand of the worker or by equipment (such as scissors), or the like.

Specific examples of the action include the following examples.

Speaking while holding the branch by hand.
Speaking a predetermined word while holding the branch by hand.
Making a predetermined sound while holding the branch by hand (such as a sound of hitting the tree and a sound of scissors for berry thinning).
Performing a predetermined gesture that can be recognized in the captured image while holding the branch by hand (such as putting the other hand into the angle of view and putting the scissors into the angle of view).
Performing a predetermined gesture that can be detected by the sensor unit 7 while holding the branch by hand (such as hitting the ground by leg and shaking the other hand (detected based on vibration or pressure)).

Note that, depending on whether or not the worker rotates the bunch of grapes, a process similar to the second embodiment can be executed.

5. Processing Example of Fourth Embodiment

The pieces of grapes are three-dimensionally arranged around the branch, and the accurate number of pieces cannot be figured out only from the captured image in one direction. Therefore, the measurement is performed based on the images of a plurality of frames at the time of the rotation of the bunch of grapes in the first embodiment.

However, there is also a case of performing the measurement based on imaging in one direction. In that case, a product of the number of pieces measured from the image in one direction and a predetermined coefficient value can be calculated to estimate and measure the number of pieces in the bunch. Such an example is illustrated as a fourth embodiment to illustrate a processing example in FIG. 11.

Figure 11:
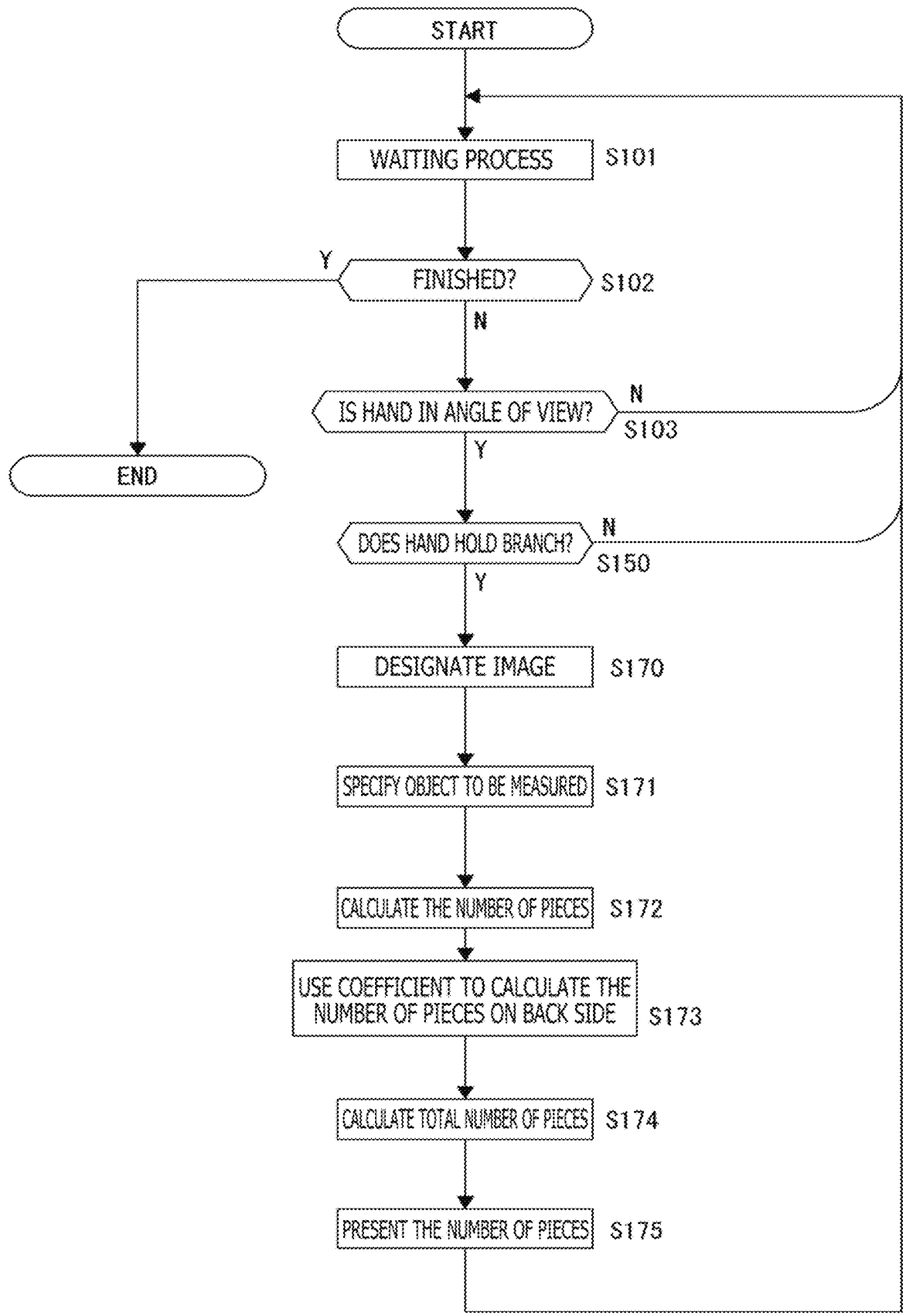
FIG. 11 is a flow chart of a processing example in a fourth embodiment.

The control unit 5 executes the waiting process in step S101 of FIG. 11 and monitors for the end of the process in step S102. The control unit 5 monitors whether or not the hand of the worker enters the angle of view in step S103.

Furthermore, once the control unit 5 detects that the hand enters the angle of view, the control unit 5 proceeds to step S150 and determines whether or not the hand holds the branch.

Furthermore, when the hand appearing in the angle of view does not hold the branch, the control unit 5 returns to step S101. When the control unit 5 detects that the hand holds (grasps) the branch, the control unit 5 regards the detection as a trigger for starting the measurement and executes the number-of-pieces measurement process from step S170.

The control unit 5 designates a captured image of a frame in step S170 and executes a process of specifying the object to be measured in the image in step S171. For example, the control unit 5 instructs the image analysis unit 4 to specify, as the object to be measured, the bunch of grapes in which the branch is held by the hand of the worker. The image analysis unit 4 determines the area (pixel area) of the bunch positioned below the hand of the worker in the image of one frame based on image analysis, luminance edge detection, color determination, or the like and specifies the pixel range of the bunch of grapes as the object to be measured.

In step S172, the control unit 5 (or the image analysis unit 4) measures the number of pieces of grapes in the pixel range as the measurement object, and the control unit 5 obtains a measurement result.

That is, the control unit 5 determines the image of the pieces in the pixel range specified as the object to be measured and measures the number of pieces.

In step S173, the control unit 5 multiplies the acquired measurement result by a preset coefficient. The number of pieces measured from the image is the number of pieces on the front side appearing as a subject of the imaging unit 2 during imaging. On the other hand, the coefficient is, for example, a coefficient for estimating the number of pieces on the back side not appearing in the captured image. Therefore, the measured number of pieces is multiplied by the coefficient to estimate the number of pieces on the back side.

In step S174, the control unit calculates the number of pieces of the entire bunch from the measured number of pieces on the front side and the number of pieces on the back side estimated by the coefficient multiplication. In this way, the measurement result of the bunch of grapes as the object to be measured is obtained.

Furthermore, the control unit 5 in step S175 executes the number-of-pieces presentation process. For example, the control unit 5 instructs the display control unit 8 to cause the display unit 9 (for example, the on-glass display unit 13) to execute the number-of-pieces display 25 as illustrated in FIG. 5.

In this way, the number of pieces can be measured rather accurately even in a case where the worker does not rotate the bunch of grapes.

However, the number of pieces on the back side is an estimated value, and the error becomes large depending on the coefficient. Therefore, the variety, the season, the location, the weather conditions, and the like can be taken into account to select an optimal coefficient.

6. Processing Example of Fifth Embodiment

Figure 12:
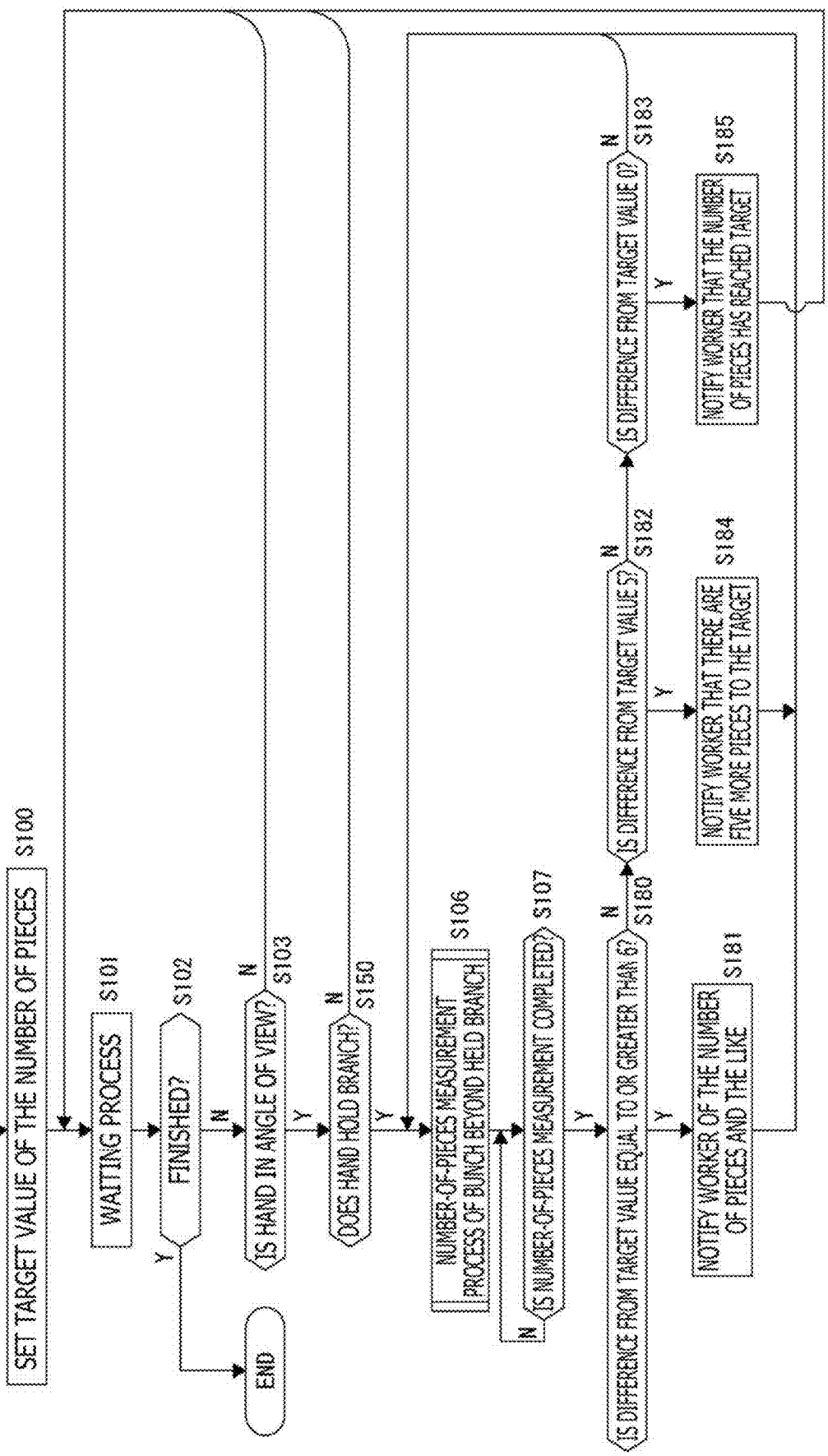
FIG. 12 is a flow chart of a processing example in a fifth embodiment.

A fifth embodiment includes a function of setting a target value of the number of pieces and provides a function of notifying the worker of information of difference from the target value or the fact that the value has reached the target value. FIG. 12 illustrates a processing example of the fifth embodiment. FIG. 12 is a processing example executed by the control unit 5 using the functions of the measurement object specification unit 5a, the measurement unit 5b, the presentation control unit 5c, and the target setting unit 5d of FIG. 2.

In step S100, the control unit 5 sets the target value of the number of pieces. For example, the control unit 5 determines the target value on the basis of an input operation of the target number of pieces input by the worker and stores the target value in the storage unit 10. For example, "35 pieces" or the like is set as the target value.

The control unit 5 executes the waiting process in step S101 and monitors for the end of the process in step S102. The control unit 5 monitors whether or not the hand of the worker enters the angle of view in step S103.

Once the control unit 5 detects that the hand enters the angle of view, the control unit 5 proceeds to step S150 and determines whether or not the hand holds the branch.

Furthermore, when the hand appearing in the angle of view does not hold the branch, the control unit 5 returns to step S101. When the control unit 5 detects that the hand holds (grasps) the branch, the control unit 5 regards the detection as a trigger for starting the measurement and proceeds to step S106 to start the number-of-pieces measurement process. The process is executed as in, for example, FIG. 8. In this case, although the worker can rotate the bunch of grapes to accurately measure the number-of-pieces from the images of a plurality of frames, the measurement algorithm may also be switched depending on whether or not the worker rotates the bunch of grapes. For example, the measurement algorithm of using a plurality of frames and the algorithm of using one frame and the coefficient for estimating the number of pieces on the back side may be switched depending on whether or not the worker rotates the bunch of grapes.

Note that, during the measurement, the display can also be performed as in, for example, FIG. 13A.

For example, the number-of-pieces display 25 is not displayed because the numerical value is still being measured.

The set target value (for example, "35") is displayed in target display 26.

"Measuring" is displayed in status display 27.

The display can be performed in this way to allow the worker to clearly recognize the target value.

Once the number-of-pieces measurement process is completed, the control unit 5 proceeds from step S107 to S180.

In step S180, the control unit 5 compares the number of pieces obtained in the number-of-pieces measurement process and the stored target value and determines whether or not the difference is equal to or greater than six.

If the difference is equal to or greater than six, the control unit 5 proceeds to step S181 and executes a process of presenting the number of pieces and the like to the worker. For example, the control unit 5 generates information, such as the number of pieces, the target value, the status, and the situation, and transmits the information to the display control unit 8 to cause the display unit 9 to display the information.

For example, FIG. 13B illustrates a display example of the display unit 9. The measurement value (for example, "45") is displayed in the number-of-pieces display 25. The set target value (for example, "35") is displayed in the target display 26. "Measurement Completed" is displayed in the status display 27. The current situation is displayed in situation display 28. In this case, the number of pieces is still large, and "Too Many" is displayed.

The display can be performed in this way to allow the worker to clearly recognize the situation of the current number of pieces and the target value.

Furthermore, the control unit 5 returns to step S106 and executes the number-of-pieces measurement process again. That is, after the worker starts the berry thinning work, the number-of-pieces measurement process is repeatedly executed.

Every time the measurement of the number of pieces is completed, the process from step S180 is executed.

Furthermore, in a case where the difference from the target value is not equal to or greater than six (that is, equal to or smaller than five) in step S180, the control unit 5 proceeds to step S182. In a case where the difference is five, the control unit 5 proceeds to step S184.

In this case, the control unit 5 instructs the display control unit 8 to execute display for the worker by displaying that there are five more pieces to the target. For example, the control unit 5 causes the display control unit 8 to execute display with content as illustrated in FIG. 13C (note that FIG. 13C and FIG. 13D illustrate only the presented content part based on the measurement).

That is, the control unit 5 causes the display control unit 8 to display the measurement value "40" in the number-of-pieces display 25, display the target value "35" in the target display 26, and display "Measurement Completed" in the status display 27. Furthermore, the control unit 5 causes the display control unit 8 to display "5 More Pieces" or the like in the situation display 28.

The process of the control unit 5 returns to step S106, and the number-of-pieces measurement process is repeated.

In this way, the remaining number of pieces can be displayed when the remaining number approaches the target, and guidance suitable for the worker can be realized.

Note that, although the display is performed here at the timing that there are five more pieces to the target, there can obviously be various types of timing, and "3 More Pieces" or the like may be displayed at the timing that the remaining number of pieces is three.

In each case where the difference is four, three, two, or one in the example of the drawings, the case does not correspond to the determination of steps S182 and S183, and the control unit 5 returns to step S106 without particularly issuing a notification.

However, in a case where the control unit 5 determines that the difference is equal to or smaller than five in step S180, the remaining number of pieces may be displayed regardless of the number of pieces indicated by the difference. In this way, the remaining number of pieces may change as in, for example, countdown display.

When the difference is zero in the calculation of the difference at the completion of the measurement, that is, when the number of pieces reaches the target value, the process of the control unit 5 proceeds from step S183 to S185, and the control unit 5 controls the display control unit 8 to notify that the number of pieces has reached the target. For example, the control unit 5 causes the display unit 9 to display the measurement value "35" in the number-of-pieces display 25, display the target value "35" in the target display 26, display "Measurement Completed" in the status display 27, and display "Target Number Reached" in the situation display 28 as illustrated in FIG. 13D.

Furthermore, this completes the berry thinning work for the bunch, and the process of the control unit 5 returns to the waiting process of step S101.

The process of FIG. 12 allows the worker to accurately execute the berry thinning for the target number of pieces. As a result, the worker can perform appropriate berry thinning work even if the worker is not an expert or can perform appropriate berry thinning work regardless of the physical condition.

Meanwhile, the measurement process can be continuously executed during the berry thinning work as in the example to provide guidance for the sections to be thinned out according to the remaining number of pieces.

For example, the current image can be analyzed while figuring out the difference value to thereby provide guidance for the pieces to be thinned out so that the density becomes rather uniform.

Figure 14:
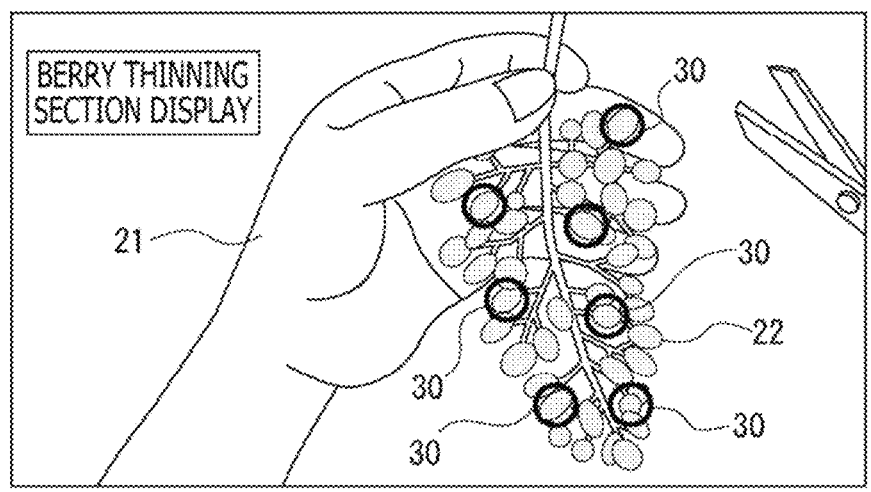
FIG. 14 is an explanatory diagram of a display example for supporting berry thinning in the embodiments.

FIG. 14 is an example of designating the pieces to be thinned out illustrated in berry thinning section display 30 for guidance. For example, an algorithm is provided to select a part crowded with pieces as a part to be preferentially thinned out. The pieces to be thinned out are selected based on the remaining number of pieces to be thinned out and the density of the pieces, and the selected pieces are presented in the berry thinning section display 30.

The pieces to be cut off can be indicated in this way to allow even an inexperienced worker to provide the pieces with rather uniform density after the berry thinning.

7. Examples of Apparatus and System Configuration

Although the embodiments have been described so far according to the configuration example of FIGS. 1 and 2, there can be various configuration examples of the apparatus and the system of the measurement apparatus 1. The configuration examples will be illustrated below.

FIG. 15A is an example of a measurement system including a glass unit 11A and an information processing apparatus 50. The information processing apparatus 50 can be a mobile terminal, such as a smartphone and a tablet.

FIG. 15B is also an example of a measurement system including the glass unit 11A and the information processing apparatus 50, and the information processing apparatus 50 can be a notebook or desktop personal computer.

For example, in a case of the configurations of FIGS. 15A and 15B, the operation of capturing the image, the specification process of the object to be measured, the measurement process, and the presentation operation of the measurement result and other information can be in the following operation modes (M1) to (M10).

Note that in each case, various sensors as the sensor unit 7 may be mounted on either one of the glass unit 11A side and the information processing apparatus 50 side. The mounted location may vary depending on the type of sensor. The detection information of various sensors can be acquired (detected or received) on the apparatus side that executes the process of specifying the object to be measured and the measurement process.

(M1)

The glass unit 11A captures an image and transmits the image to the information processing apparatus 50.

The information processing apparatus 50 executes the process of specifying and measuring the object to be measured and further presents the measurement result and the like.

(M2)

The glass unit 11A captures an image and transmits the image to the information processing apparatus 50.

The information processing apparatus 50 executes the process of specifying and measuring the object to be measured and transmits the information of the measurement result and the like to the glass unit 11A.

The glass unit 11A side presents the measurement result and the like.

(M3)

The glass unit 11A captures an image and executes the process of specifying and measuring the object to be measured. Furthermore, the glass unit 11A transmits the information of the measurement result and the like to the information processing apparatus 50.

The information processing apparatus 50 presents the measurement result and the like.

(M4)

The glass unit 11A captures an image and specifies the object to be measured. The glass unit 11A transmits the captured image and the information indicating the specified object to be measured to the information processing apparatus 50.

The information processing apparatus 50 executes the measurement process and further presents the measurement result and the like.

(M5)

The glass unit 11A captures an image and specifies the object to be measured. The glass unit 11A transmits the captured image and the information indicating the specified object to be measured to the information processing apparatus 50.

The information processing apparatus 50 executes the measurement process and transmits the measurement result to the glass unit 11A.

The glass unit 11A side presents the measurement result and the like.

(M6)

The information processing apparatus 50 captures an image and transmits the image to the glass unit 11A.

The glass unit 11A executes the process of specifying and measuring the object to be measured and further presents the measurement result and the like.

(M7)

The information processing apparatus 50 captures an image and transmits the image to the glass unit 11A.

The glass unit 11A executes the process of specifying and measuring the object to be measured and transmits the information of the measurement result and the like to the information processing apparatus 50.

The information processing apparatus 50 side presents the measurement result and the like.

(M8)

The information processing apparatus 50 captures an image and executes the process of specifying and measuring the object to be measured. The information processing apparatus 50 transmits the information of the measurement result and the like to the glass unit 11A.

The glass unit 11A side presents the measurement result and the like.

(M9)

The information processing apparatus 50 captures an image and specifies the object to be measured. The information processing apparatus 50 transmits the captured image and the information indicating the specified object to be measured to the glass unit 11A.

The glass unit 11A executes the measurement process and further presents the measurement result and the like.

(M10)

The information processing apparatus 50 captures an image and specifies the object to be measured. The information processing apparatus 50 transmits the captured image and the information indicating the specified object be measured to the glass unit 11A.

The glass unit 11A executes the measurement process and transmits the measurement result and the like to the information processing apparatus 50.

The information processing apparatus 50 side presents the measurement result and the like.

Although the examples are illustrated above, there can be various examples of operation that can be performed by combining a user-mounted device, such as the glass unit 11A, and the information processing apparatuses 50.

Obviously, these are examples. For example, when the acquisition of information and the handling of information in the process of the sensor unit 7, the mode of the operation unit 6, and the like are taken into account, there can be various other examples.

Figure 16:
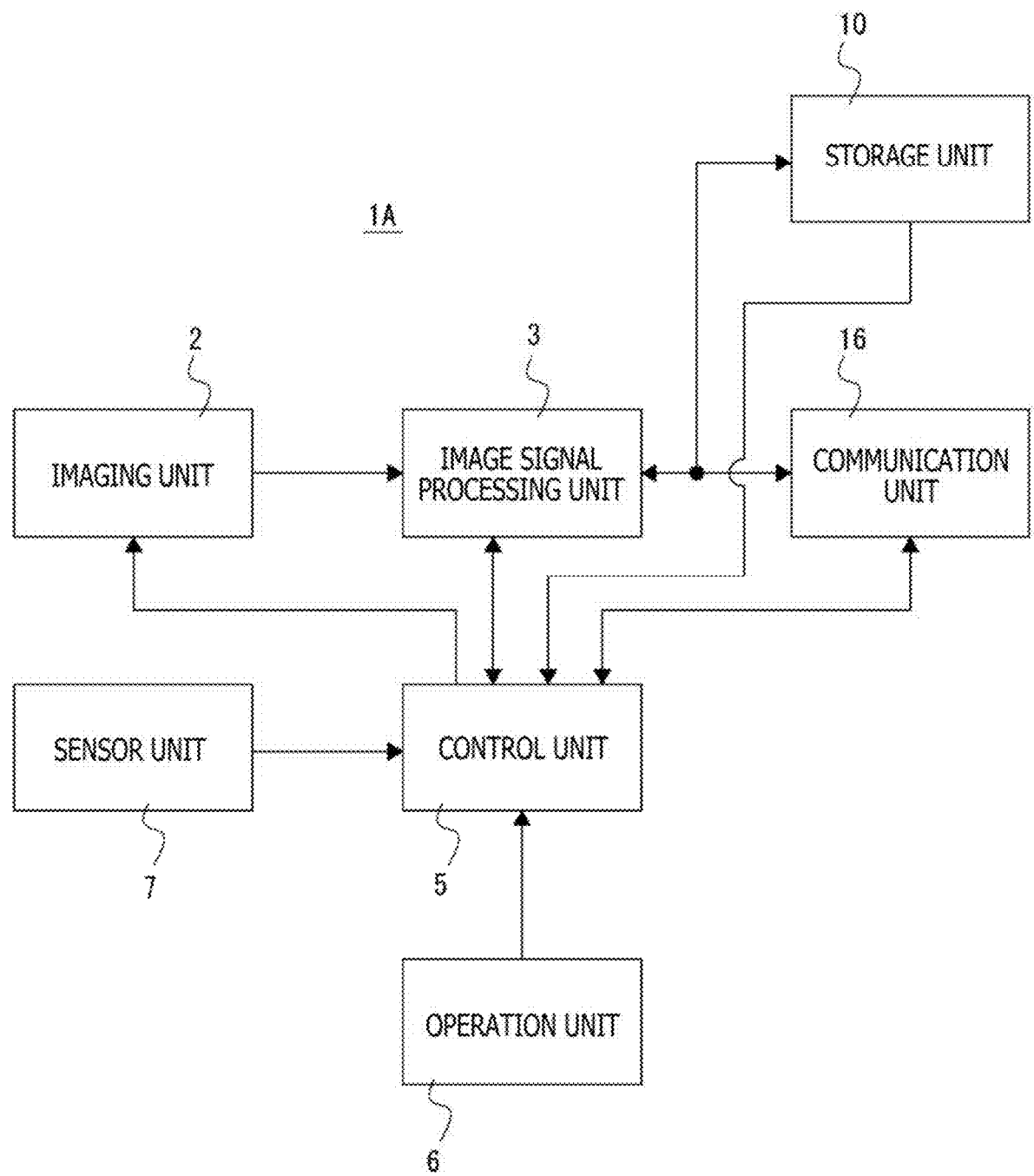
FIG. 16 is a block diagram of a configuration example of a measurement terminal in the embodiments.

For example, in a case of each mode described above, the measurement system includes the glass unit 11A and the information processing apparatus 50, and the glass unit 11A functions as a measurement terminal. In a case of the operation mode of (M1), an example of the configuration of a measurement terminal 1A includes the configuration as illustrated in FIG. 16.

The measurement terminal 1A includes the imaging unit 2, the image signal processing unit 3, the control unit 5, the operation unit 6, the sensor unit 7, the storage unit 10, and a communication unit 16.

That is, the measurement terminal 1A does not include the image analysis unit 4, the display control unit 8, and the display unit 9 in the configuration of FIG. 1 and includes the communication unit 16.

The imaging unit 2, the image signal processing unit 3, the control unit 5, the operation unit 6, the sensor unit 7, and the storage unit 10 are similar to the ones described in FIG. 1. However, in a case of the mode of (M1), the control unit 5 may not have the functional configuration as illustrated in FIG. 2.

The communication unit 16 performs wired or wireless data communication or network communication with an external device. In the cases of the modes (M1) to (M10), the communication unit 16 is provided to communicate with the information processing apparatus 50. For example, an example of the communication unit 16 includes a short-range wireless communication unit of Bluetooth (registered trademark) or the like.

Note that the communication unit 16 as a network communication unit may perform communication using various networks, such as, for example, the Internet, a home network, and a LAN (Local Area Network), and may transmit and receive various types of data to and from a server, a terminal, and the like on the network.

In the case of the operation mode of (M1), the glass unit 11A can have the configuration of FIG. 16.

In the glass unit 11A of the case of the operation mode of (M2), the control unit 5 can have the function of the presentation control unit 5c, and the display control unit 8 and the display unit 9 of FIG. 1 can be added in the configuration of FIG. 16.

In the glass unit 11A of the case of the operation mode of (M3), the control unit 5 can have the functions of the measurement object specification unit 5a and the measurement unit 5b, and the image analysis unit 4 can be included in the configuration of FIG. 16.

In the glass unit 11A of the case of the operation mode of (M4), the control unit 5 can have the function of the measurement object specification unit 5a, and the image analysis unit 4 can be included in the configuration of FIG. 16.

In the glass unit 11A of the case of the operation mode of (M5), the control unit 5 can have the functions of the measurement object specification unit 5a and the presentation control unit 5c, and the image analysis unit 4, the display control unit 8, and the display unit 9 can be included in the configuration of FIG. 16.

In the glass unit 11A of the case of the operation mode of (M6), the control unit 5 can have the functions of the measurement object specification unit 5a and the measurement unit 5b, and the image analysis unit 4, the display control unit 8 and the display unit 9 can be added in the configuration of FIG. 16. The imaging unit 2 and the image signal processing unit 3 are not necessary.

In the glass unit 11A of the case of the operation mode of (M7), the control unit 5 can have the functions of the measurement object specification unit 5a and the measurement unit 5b, and the image analysis unit 4 can be added in the configuration of FIG. 16. The imaging unit 2 and the image signal processing unit 3 are not necessary.

In the glass unit 11A of the case of the operation mode of (M8), the display control unit 8 and the display unit 9 can be added in the configuration of FIG. 16. The imaging unit 2 and the image signal processing unit 3 are not necessary.

In the glass unit 11A of the case of the operation mode of (M9), the control unit 5 can have the function of the measurement unit 5b, and the image analysis unit 4, the display control unit 8, and the display unit 9 can be included in the configuration of FIG. 16.

In the glass unit 11A of the case of the operation mode of (M10), the control unit 5 can have the function of the measurement unit 5b, and the image analysis unit 4 can be included in the configuration of FIG. 16.

Figure 17:
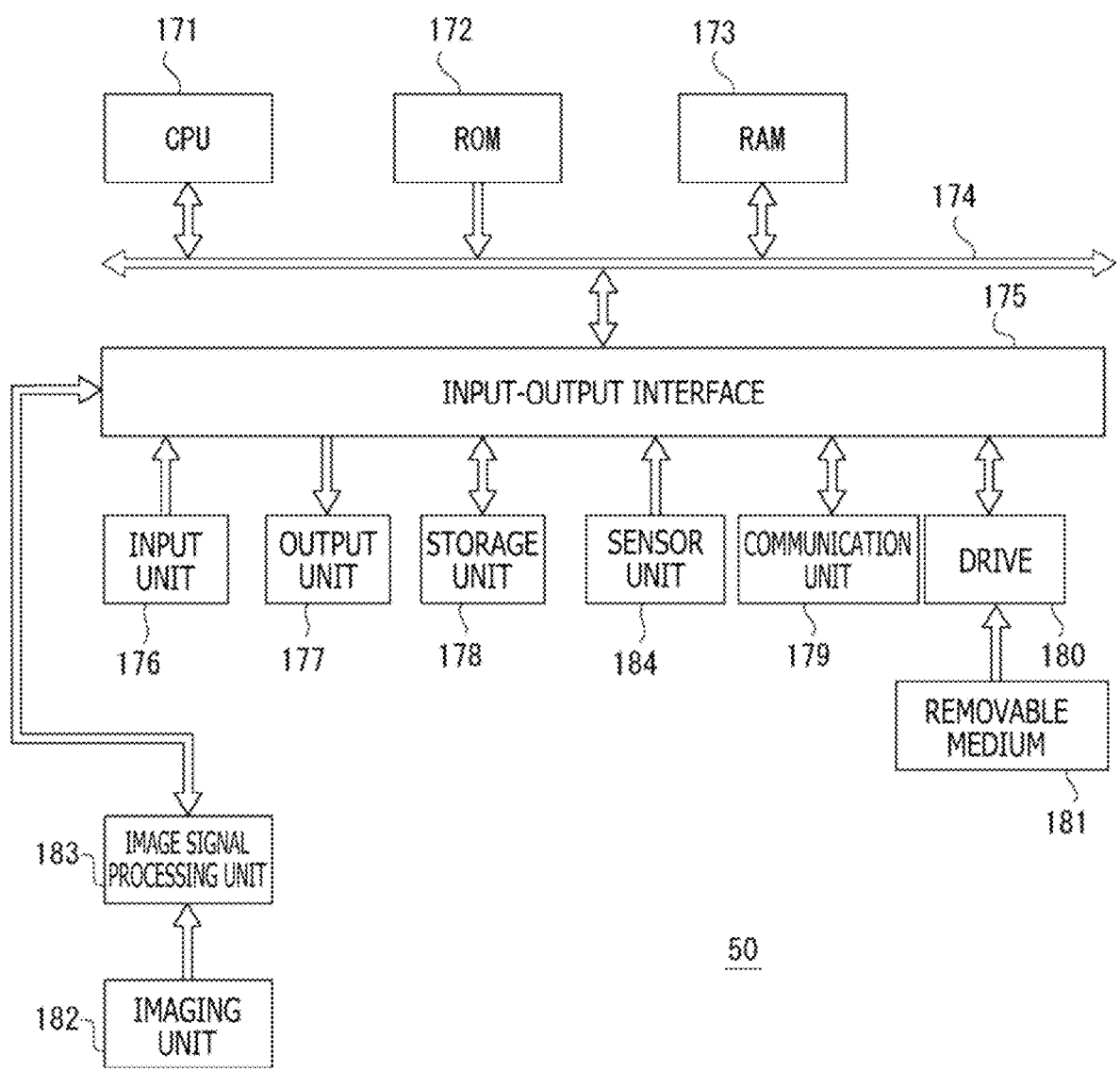
FIG. 17 is a block diagram of a configuration example of an information processing apparatus in the embodiments.

On the other hand, the hardware configuration of the information processing apparatus 50 can be realized by, for example, a configuration of a computer apparatus as illustrated in FIG. 17.

In FIG. 17, a CPU 171 executes various processes according to programs stored in a ROM 172 or programs loaded from a storage unit 178 to a RAM 173. Data and the like necessary for the CPU 171 to execute various processes are also appropriately stored in the RAM 173.

The CPU 171, the ROM 172, and the RAM 173 are connected to each other through a bus 174. An input-output interface 175 is also connected to the bus 174.

Components connected to the input-output interface 175 include: an input unit 176 including a keyboard, a mouse, a touch panel, and the like; an output unit 177 including a display, such as an LCD and an organic EL panel, a speaker, and the like; the storage unit 178 including a hard disk or the like; and a communication unit 179 including a modem or the like.

The communication unit 179 executes a communication process through a network, such as the Internet, and performs wired/wireless communication with a peripheral apparatus and communication using bus communication or the like.

In addition, the communication unit 179 is provided to communicate with the glass unit 11A in the cases of the modes of (M1) to (M10), and in these cases, the communication unit 179 can be, for example, a short-range wireless communication unit of Bluetooth or the like.

A drive 180 is also connected to the input-output interface 175 as necessary, and a removable medium 181, such as a magnetic disk, an optical disk, a magneto-optical disk, and a semiconductor memory, is appropriately mounted on the input-output interface 175. Computer programs read from them are installed on the storage unit 178 as necessary.

A sensor unit 184 is also connected to the input-output interface 175 in some cases. The sensor unit 184 can include various sensors just like the sensor unit 7 of FIG. 1.

In the cases of the modes of (M6) to (M10), the information processing apparatus 50 includes an imaging unit 182 and an image signal processing unit 183 to capture an image, and the image signal processing unit 183 is connected to the input-output interface 175. Therefore, the CPU 171 can apply various analysis processes and the like to the captured image. The imaging unit 182 and the image signal processing unit 183 are sections similar to the imaging unit 2 and the image signal processing unit 3 of FIG. 1.

Note that the imaging unit 182 and the image signal processing unit 183 are not necessary in the cases of the modes of (M6) to (M10). That is, the imaging unit 182 and the image signal processing unit 183 may not be mounted or may not be used even if they are mounted. However, the imaging unit 182 can be used as a sensor.

In the information processing apparatus 50 of FIG. 17, the configurations corresponding to the operation modes are as follows.

In the case of the operation mode of (M1), the information processing apparatus 50 can have the configuration of FIG. 17, and particularly, the CPU 171 has the functions of the measurement object specification unit 5*a*, the measurement unit 5*b*, and the presentation control unit 5*c*.

In the information processing apparatus 50 of the case of the operation mode of (M2), the CPU 171 can have the functions of the measurement object specification unit 5*a* and the measurement unit 5*b* in the configuration of FIG. 17.

In the information processing apparatus 50 of the case of the operation mode of (M3), the CPU 171 can have the function of the presentation control unit 5*c* in the configuration of FIG. 17.

In the information processing apparatus 50 of the case of the operation mode of (M4), the CPU 171 can have the functions of the measurement unit 5*b* and the presentation control unit 5*c* in the configuration of FIG. 17.

In the information processing apparatus 50 of the case of the operation mode of (M5), the CPU 171 can have the function of the measurement unit 5*b* in the configuration of FIG. 17.

In the case of the operation mode of (M6), the information processing apparatus 50 can have the configuration of FIG. 17.

In the information processing apparatus 50 of the case of the operation mode of (M7), the CPU 171 can have the function of the presentation control unit 5*c* in the configuration of FIG. 17.

In the information processing apparatus 50 of the case of the operation mode of (M8), the CPU 171 can have the functions of the measurement object specification unit 5*a* and the measurement unit 5*b* in the configuration of FIG. 17.

In the information processing apparatus 50 of the case of the operation mode of (M9), the CPU 171 can have the function of the measurement object specification unit 5*a* in the configuration of FIG. 17.

In the information processing apparatus 50 of the case of the operation mode of (M10), the CPU 171 can have the functions of the measurement object specification unit 5*a* and the presentation control unit 5*c* in the configuration of FIG. 17.

In this way, there are cases in which the CPU 171 has the functions of the measurement object specification unit 5*a*, the measurement unit 5*b*, and the presentation control unit 5*c*. Note that although not mentioned, there are also cases in which the CPU 171 has the function of the target setting unit 5*d*.

In a case where software executes the functions, a program included in the software is installed from a network or a recording medium.

The recording medium includes a removable medium 181, such as a magnetic disk, an optical disk, a magneto-optical disk, and a semiconductor memory recording the program, delivered to distribute the program to the user. Alternatively, the recording medium includes the ROM 172 recording the program, a hard disk included in the storage unit 178, or the like incorporated in advance into the body of the apparatus and distributed to the user.

In the configuration examples described above, the measurement system includes the glass unit 11A and the information processing apparatus 50 as illustrated in FIGS. 15A and 15B. The measurement system can be regarded as a system including the measurement terminal 1A as a wearable (body-mounted) unit and the information processing apparatus 50. The body-mounted unit is a unit that can be mounted on the body of a person or on clothes.

In that sense, there can be various body-mounted units instead of the eyeglass-type glass unit 11A. For example, the body-mounted unit can be a head-mounted type, an earphone type, a wristband type, a clothes type, a clip type, a pocket storage type, a pendant type, or the like.

FIG. 15C illustrates a case in which the information processing apparatus 50 as a mobile terminal, such as, for example, a smartphone, is the measurement apparatus 1 of the embodiments.

For example, the information processing apparatus 50 has the configuration similar to FIG. 1, and the worker uses the information processing apparatus 50 (smartphone) to image the grapes. Furthermore, the processes as in the first to fourth embodiments are executed to perform the measurement, and the number-of-pieces display 25 as a measurement result is performed as illustrated in FIG. 18A.

Figure 18:
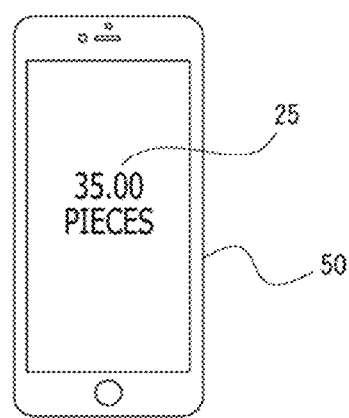
FIG. 18 is an explanatory diagram of modes and display examples of the measurement apparatus using a mobile terminal in the embodiments.
Figure 18:
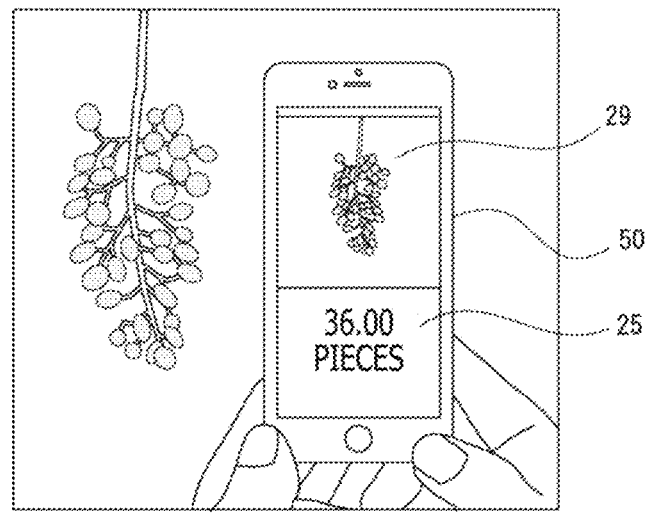

As illustrated in FIG. 18B, both of captured image display 29 and the number-of-pieces display 25 as a measurement result may be displayed.

FIG. 15D illustrates a case in which the measurement system includes an imaging apparatus 60 and the information processing apparatus 50. However, the imaging apparatus 60 is a normal video camera, and the information processing apparatus 50 substantially functions as the measurement apparatus 1.

That is, the information processing apparatus 50 uses the captured image transmitted by communication to perform the operation of the measurement apparatus 1 (processes of the first to fourth embodiments).

In this way, the imaging apparatus 60 and the information processing apparatus 50 can be combined to provide the measurement system.

Figure 19:
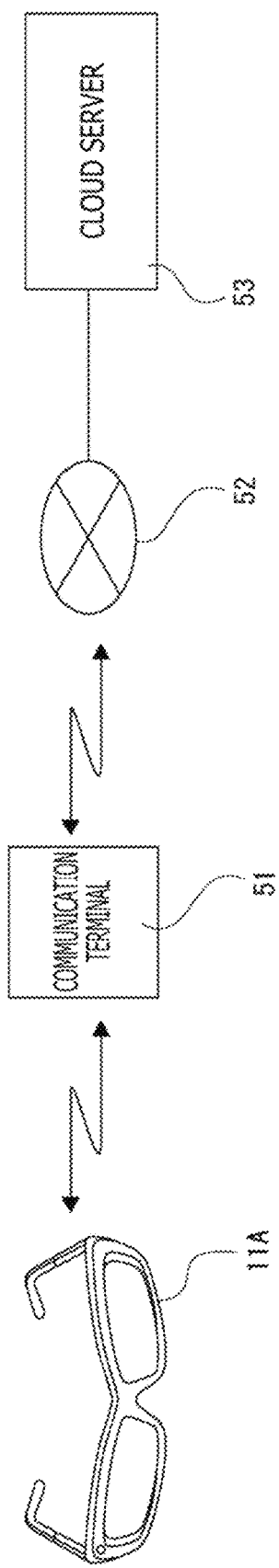
FIG. 19 is an explanatory diagram of modes of a measurement system using network communication in the embodiments.
Figure 19:
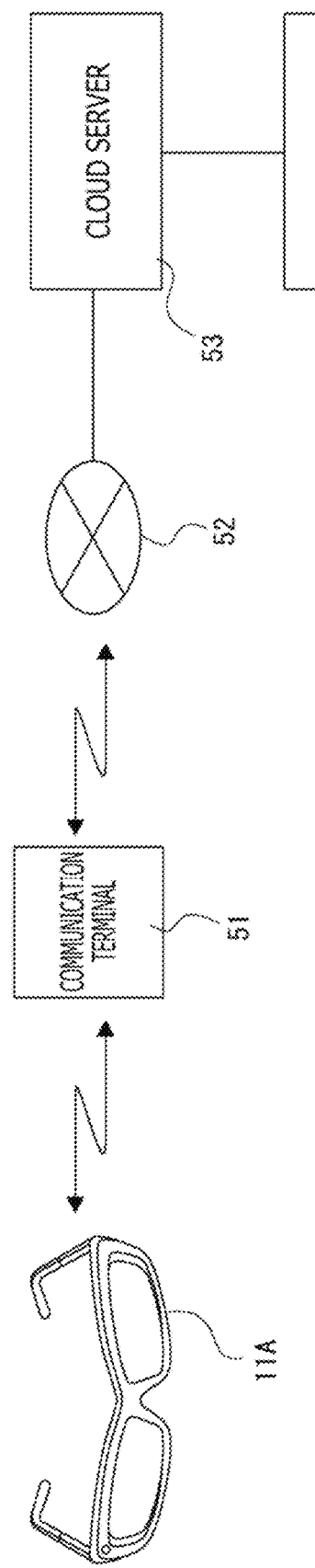

FIG. 19 illustrates a configuration of the measurement system through network communication.

FIG. 19A illustrates the glass unit 11A, a communication terminal 51, a network 52, and a cloud server 53.

Examples of the network 52 include various modes, such as the Internet, a LAN, a VPN (Virtual Private Network), an intranet, an extranet, a satellite communication network, a CATV (Community Antenna Tele Vision) communication network, a telephone network, and a mobile communication network.

The cloud server 53 includes an information processing apparatus. The cloud server 53 and the communication terminal 51 are realized by, for example, the computer apparatus as illustrated in FIG. 17.

The glass unit 11A transmits the captured image and the sensor information to the communication terminal 51. The communication terminal 51 is, for example, a smartphone, a tablet, a dedicated terminal, or the like and is an information processing apparatus capable of network connection. The captured image, the sensor information, and the like from the glass unit 11A are transmitted from the communication terminal 51 to the cloud server 53 through the network 52.

In this case, the cloud server 53 has the functions of the measurement object specification unit 5a and the measurement unit 5b, so that the cloud server 53 measures the number of pieces and returns the measurement result. The glass unit 11A receives the measurement result through the network 52 and the communication terminal 51 and displays the measurement result.

In this way, the measurement system can also be constructed by a so-called cloud service.

FIG. 19B is a diagram including an AI engine 54 added to the configuration of FIG. 19A. The AI engine 54 executes the measurement object specification process and the measurement process based on image analysis.

In this way, highly accurate measurement process, determination for executing the measurement, and the like can be performed.

Note that the glass unit 11A as a body-mounted unit may be able to directly perform network communication, and the communication terminal 51 may not be provided.

8. Conclusion and Modifications

The embodiments have been described, and according to the embodiments, the following advantageous effects can be obtained.

The measurement apparatus 1 of the embodiments include: the measurement object specification unit 5a that executes the process of specifying the object to be measured based on the detection of the grasping of the branch (object) of grapes by the hand (gripper) of the worker; and the measurement unit 5b that obtains the measurement result in the measurement process of the feature amount of the object to be measured specified by the measurement object specification unit 5a.

That is, in the embodiments, the action of grasping the branch by the gripper, such as the hand of the worker, is detected to specify the object to be measured. In other words, the branch of a bunch of grapes is held to specify the bunch of grapes as an object to be measured, and the feature amount, such as the number of pieces, is measured.

In this way, the object to be measured can be clearly specified in the course of the work with an opportunity of grasping an object. For example, the range to be measured in the captured image becomes clear.

In addition, the action of grasping the branch by hand is part of the work (for example, berry thinning) to be executed or is an action leading to the work. Therefore, the object to be measured can be accurately specified in a natural flow of work. As a result, the object to be measured for providing information necessary for the worker can be correctly set and measured without requesting the worker for some extra action, operation, or the like. This improves the usability and contributes to making the berry thinning work efficient. The measurement accuracy is also improved.

In addition, a large number of bunches of grapes appear in the captured image. In that case, the process may become unstable in determining the part of the image for which the number of pieces is to be measured. However, the branch is held in the course of the work to specify the bunch to be measured in the present embodiments, and the number of pieces in the bunch desired by the worker can be correctly set as the object to be measured in the course of the normal work performed by the worker. Particularly, in the case of crops of fruit, such as grapes and bananas, grown in bunches, it is significantly useful that the bunch to be measured is specified by grasping the bunch.

Although the grapes are illustrated as an example of the object to be measured in the embodiments, the present technique can be applied to the measurement of various objects, such as crops like bananas and tomatoes, natural objects like trees and animals, and industrial products. Among the various objects, the object to be measured is all or part of the objects specified by grasping.

In addition, although the feature amount is the number of pieces, the feature amount can be a value that can be quantified, compared, and evaluated, such as dimension (size), color, component content, component ratio, sugar content, moisture content, and estimated price, other than the number of pieces. The present technique can also be widely applied as a measurement apparatus of these.

The measurement apparatus 1 of the embodiments includes the presentation control unit 5c that executes the process for presentation based on the measurement result.

Therefore, the worker can recognize the information, such as, for example, the number of pieces in the bunch of grapes in which the branch is held. That is, the measurement apparatus 1 can provide appropriate information in the course of the work of the worker.

Note that the value presented based on the measurement result is not limited to, for example, the value of the measurement result of the feature amount, and proper/improper determination information, guide information, or the like corresponding to the measurement result may be presented. For example, instead of the numerical value as a measurement result, determination information, such as "proper," "improper," "appropriate quantity," "insufficient," and "excessive," or guide content for subsequent work can be presented to support accurate work.

In addition, although the sound output unit, the vibration unit, and the like are illustrated as examples of the presentation device in addition to the display unit 9, the presentation control unit 5c can control the presentation devices to present the measured feature amount in presentation modes corresponding to the presentation devices.

The captured image is used to execute the measurement process in the examples illustrated in the embodiments. For example, the integrated or separate imaging unit 2 images the object, and the captured image is input. Furthermore, the input captured image is used to measure the feature amount that can be determined from the image.

The captured image can be analyzed to measure the feature amount, such as, for example, the number of pieces of grapes. One or a plurality of frames of the captured images can be used to perform stable measurement, and the measurement accuracy can be improved.

Note that not only the captured image, but also the detection information of the sensor unit 7 can be used to perform the measurement.

The measurement process is executed based on the detection of the grasping of the object by the gripper in the examples described in the embodiments (see FIGS. 9 and 11). That is, the measurement of the feature amount of the object to be measured is started by the detection of the grasping of the object by the gripper.

The feature amount of the object to be measured is measured in a case where the object to be measured is specified based on grasping, and the measurement requested by the worker is executed without a special operation of the worker (operation of instructing to start the measurement).

Particularly, the operation of holding the branch of the bunch is an operation in the normal flow of work in the berry thinning work of grapes. Therefore, the measurement is executed at appropriate timing without the worker being conscious of the measurement operation, and this significantly improves the usability.

In addition, depending on the object to be measured or the feature amount to be measured, the object does not have to be rotated or vertically moved in the grasped state. In that case, appropriate start timing of measurement can be obtained by grasping.

The measurement process is executed based on the detection of the grasping of the object and the moving of the object by the gripper in the examples described in the embodiments (see FIG. 8).

For example, the measurement of the feature amount of the object to be measured is started when some motion is applied to the object in the grasped state. The movement can be shaking, holding and moving up, down, left, right, back, and forth, shaking, rotating, or the like.

The movement of the object to be measured is necessary in some cases to measure the object to be measured. For example, in a case of measuring the number of pieces of grapes, not only the pieces on the front side as viewed from the worker, but also the pieces on the back side need to be counted, and the object needs to be rotated. Therefore, the movement (for example, rotation of bunch) in addition to grasping may be a natural operation in the work. In that case, the measurement is performed after the detection of the holding operation and the movement, and the measurement is accurately executed when needed. In addition, a special operation of the worker (operation of instructing to start the measurement) is not necessary, and there is no operation load.

Furthermore, moving the object in the grasped state (for example, moving the object up, down, left, right, back, and forth, shaking the object, or rotating the object in the holding state) can also be considered as a deliberate measurement start operation of the worker. In that case, a simple operation continued from grasping can be performed to instruct the apparatus to start the measurement. This is suitable in a case where, for example, the measurement is to be triggered by something in addition to holding the object.

The measurement process is executed based on the detection of the grasping of the object by the gripper and a predetermined action other than the grasping in the examples described in the embodiments (see FIG. 10).

For example, a predetermined action in the state in which the gripper grasps the object is detected to start the measurement of the feature amount of the object to be measured. The predetermined action can be an audio action, such as a speech of the worker and generation of a predetermined sound, a gesture action by the hand of the worker or by equipment (such as scissors), or the like.

The predetermined action of the worker in the grasped state is regarded as an operation for starting the measurement. This allows the worker to instruct the apparatus to start the measurement at appropriate timing in the grasped state. Particularly, the predetermined action is an action other than the action of the gripper, and the worker can easily issue an instruction in the grasped (branch of the grapes is held) state. Specifically, the predetermined action can be a speech of the worker, a speech of a predetermined word by the worker, generation of a sound (action of generating some sound by the hand other than the hand holding the object or by a thing held in the hand), or the like, and the work is not obstructed. In addition, the predetermined action can also be putting the hand other than the hand holding the branch into the image and performing a predetermined gesture, putting the scissors held in the other hand into the angle of view of the imaging unit 2, performing a predetermined gesture, or the like. In this case, the predetermined action is also an operation without a load in the work.

In the examples illustrated in the embodiments, the measurement process is executed by using the images of the plurality of frames captured in the period in which the object to be measured is moved (see FIG. 8).

For example, the captured images of the object imaged by the imaging unit 2 are input, and a plurality of frames of the images obtained as moving images are used to perform the measurement. The images of a plurality of frames in the course of the movement of the object to be moved can be used to accurately detect the feature amount even in a case where, for example, there are front and back sides. In the cases of the number of pieces of grapes, the images captured while the grapes are rotated can be used to measure the pieces on the front side and the pieces on the back side. This can improve the measurement accuracy.

In the examples described in the embodiments, the measurement object specification unit 5a executes the process of setting, as the object to be measured, the object grasped and moved by the gripper (see FIG. 6).

For example, the measurement object specification unit 5a sets, as the object to be measured, an object or part of the object applied with some motion in the grasped state. Examples of the movement include holding the object to move the object up, down, left, right, back, and forth, shaking the object, rotating the object, and the like.

The object to be moved can be specified by moving the object (for example, rotating the bunch) in addition to grasping the object, and the moved object or part of the object can be set to more accurately specify the object or part (or range) of the object to be measured.

In the case of the grapes, the rotated bunch, the picked up bunch, or the like can be set to further limit the measurement object to accurately specify the measurement object.

The target setting unit 5d that sets the target value of the feature amount is provided in the embodiments, and the target setting unit 5d obtains the difference value of the feature amount measured in the measurement process and the target value (see FIG. 12).

For example, the target value of the feature amount is set and stored based on user settings, automatic settings, or the like to allow comparing the target value and the measurement value. For example, in the case of setting the number of pieces as a target value in the berry thinning work, the number of pieces and the measured number of pieces can be compared to obtain difference information indicating the amount of pieces to be further thinned out.

Figure 13:
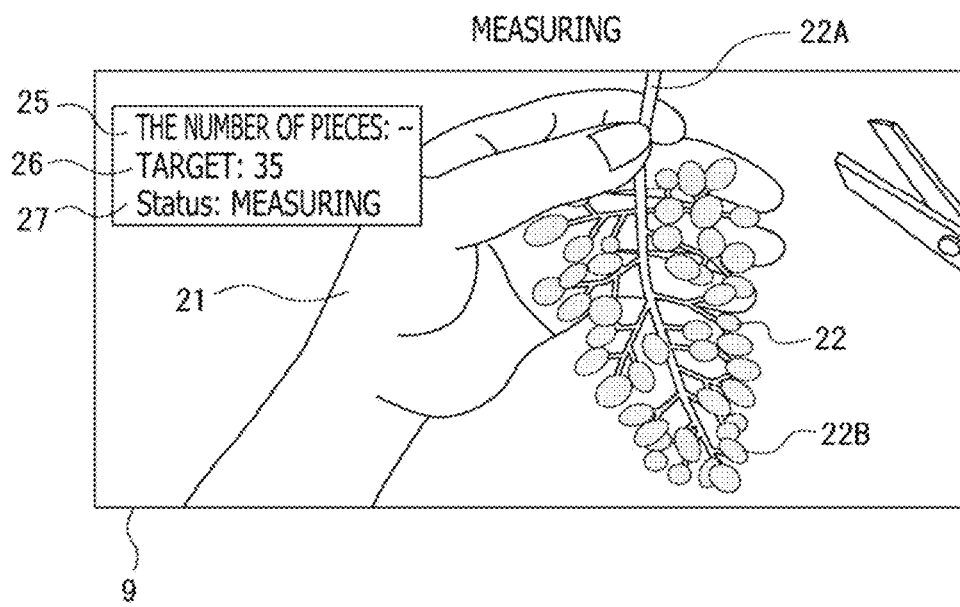
FIG. 13 is an explanatory diagram of a display example in the fifth embodiment.
Figure 13:
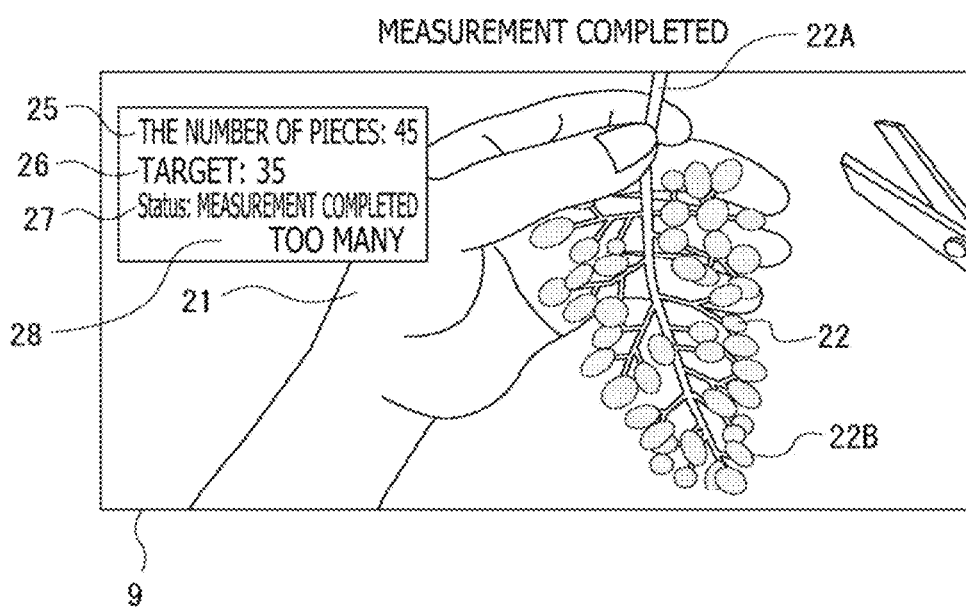
Figure 13:
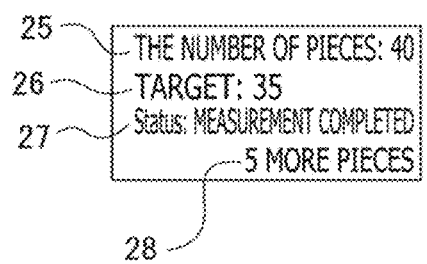
Figure 13:
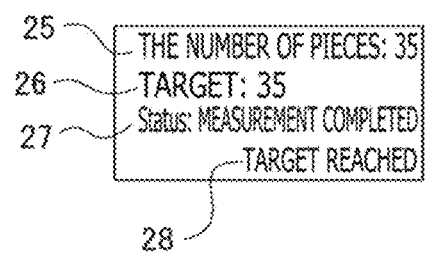

The presentation control unit 5c that executes the process for presenting the difference value of the feature amount measured in the measurement process and the target value is provided in the embodiments (see FIGS. 12 and 13). The presentation control unit 5c uses the method of display, sound, or the like to present the difference between the current feature amount and the target value.

For example, in a case where the difference information indicating the amount of pieces to be further thinned out is obtained, the presentation control unit 5c can notify the worker of the difference information to appropriately present the difference information to support the work.

Note that in this case, the pieces to be thinned out can be further presented as illustrated in FIG. 14 to support the worker, and even an inexperienced worker can accurately execute the berry thinning work.

The movement as a trigger for the measurement process is the rotational movement of the bunch of grapes in the examples illustrated in the embodiments (see FIG. 6).

For example, in the case of measuring the number of pieces of grapes, the grapes need to be rotated because not only the pieces on the front side as viewed from the worker, but also the pieces on the back side need to be counted. Therefore, rotating the bunch in addition to grasping the bunch is a natural operation in the work, and the measurement can be started once the rotation is detected. This can prevent application of unnecessary operation load on the worker.

Note that the detection of the rotational movement may be used to specify the object to be measured. In the case of the grapes, the rotated bunch can be set to further limit the measurement object to accurately specify the measurement object.

Although the gripper that grasps the object to specify the object to be measured is the hand of a person in the embodiments, the gripper may be a tool operated by a person or an automatically operated robot arm.

Examples of the hand of a person include a bare hand, a hand wearing a glove, and the like. In the case of the embodiments, grasping of the object by the hand of the worker is monitored, and the process of natural operation in the berry thinning work can be detected without using a special grasping apparatus. This prevents application of load on the worker.

The gripper can be a tool, and the tool denotes any tool that can be grasped by the intention of the person regardless of the mode, such as a tool operated by the person by hand, a tool operated by something other than the hand, a tool mounted on the hand and used, and a remotely controlled tool. The other hand holds scissors during the berry thinning work, and therefore, grasping of the object by the scissors can also be detected.

In addition, for operations other than the berry thinning of grapes, various tools may be used in the work. For a measurement apparatus related to work in which a tool is used, it is effective to detect grasping of the object by the tool to specify the object to be measured.

In addition, it is also useful in some cases to detect grasping of the object by a robot arm used for factory automation or the like to specify the object to be measured. In cases of a cultivation process of crops, a working process at the time of shipment, measurement in a distribution line, measurement in a manufacturing line or the like of processed food, measurement in a manufacturing line or the like of industrial product, and the like, the object to be measured can be specified based on grasping of the object by the robot arm. This enables accurate measurement.

In this way, the gripper can be the hand of the person, the tool, or the robot arm. That is, if the gripper can grasp the object, the object grasped by the gripper can be set as the object to be measured. As a result, various types of work can be handled, and a grasping action performed in the work can be detected to specify the object to be measured.

The object as the object to be measured is grapes, that is, crops, in the examples illustrated in the embodiments. The measurement object specification unit specifies grasped individual crops as the object to be measured among the crops. The crops are crops in a broad sense including fruits, vegetables, grains, trees, flowers, mushrooms, fertilizers, animal feed, garden crops, industrial crops, and the like.

According to the technique of the embodiments, the measurement apparatus 1 corresponding to the various crops can be widely provided.

In the examples illustrated in the embodiments, the measurement object specification unit 5a executes a process of setting, as the object to be measured, the bunch of grapes in which the branch is grasped by the gripper, and in the measurement process, the measurement object specification unit 5a measures the number of pieces as the feature amount of the bunch of grapes set as the object to be measured.

That is, the bunch of grapes in which the branch is held is set as the object to be measured, and the number of pieces in the bunch is measured.

The branch of each of a large number of bunches of grapes in the farm is held to specify the bunch to be measured, and the number of pieces in the bunch is measured. As a result, automatic measurement of the number of pieces of each bunch can be accurately performed, and the information of the number of pieces necessary for the berry thinning work of the grapes can be accurately provided to the worker. This can significantly improve the efficiency of the berry thinning work that is very cumbersome and that needs to be performed in a short period (about two weeks).

In addition, years of experience may be necessary to determine the number of pieces of grapes at a glance in the berry thinning, and the determination may become unstable depending on the physical condition. However, the number of pieces can be measured and presented to perform appropriate berry thinning work regardless of the experience or the physical condition.

The measurement apparatus 1 of the embodiments includes the imaging unit 2 that captures an image to be used in the measurement process.

The measurement unit 5b analyzes the image captured by the imaging unit 2 and measures the number of pieces. Since the imaging unit 2 is provided on the measurement apparatus 1, an imaging apparatus does not have to be separately prepared or installed, and a measurement apparatus with excellent usability can be provided in the course of the berry thinning work and the like.

Note that although the imaging unit 2 (camera 12) is integrated and embedded in the examples described in FIGS. 1 and 3, the imaging unit 2 may be provided as a separate apparatus.

Figure 15:
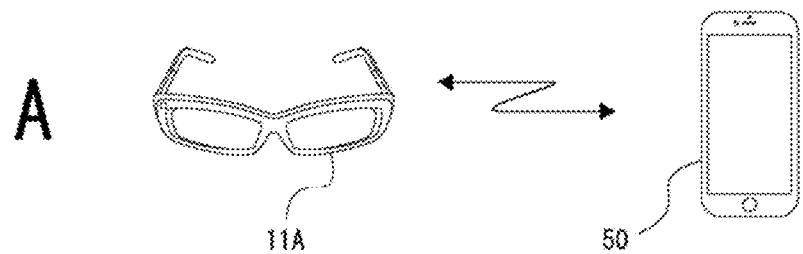
FIG. 15 is an explanatory diagram of various examples of measurement apparatuses and system configuration in the embodiments.
Figure 15:
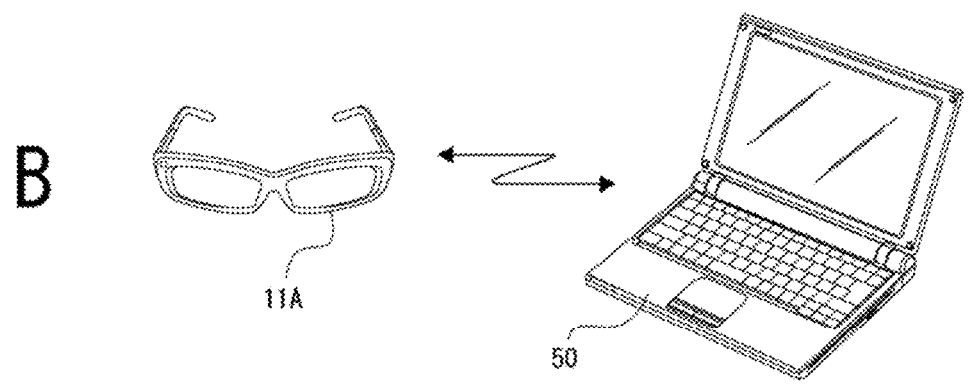
Figure 15:
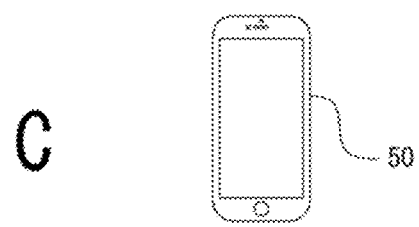
Figure 15:
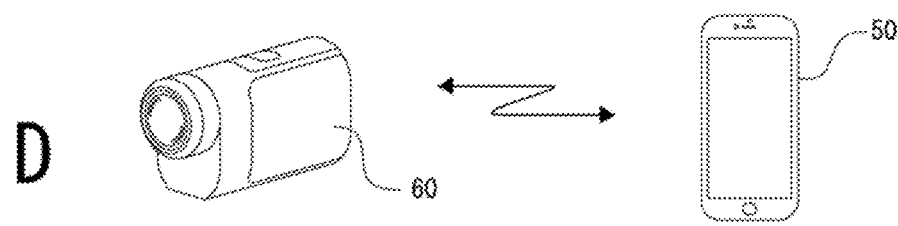

In the examples described in the embodiments, the imaging unit (camera 12) that captures the image to be used in the measurement process and the presentation unit (on-glass display unit 13) that presents the measurement result are provided, and the imaging unit and the presentation unit are arranged on the body-mounted unit (glass units 11 and 11B) (see FIGS. 3 and 15).

The imaging unit and the presentation unit are arranged on the body-mounted unit. Therefore, the worker can just wear the body-mounted unit, and the worker does not have to pay attention to the arrangement or the like of the device for imaging the object to be measured or for displaying the measurement result. Specifically, the worker can wear, for example, the eyeglass-type glass unit 11 including the camera 12 and the on-glass display unit 13 as illustrated in FIG. 3 to accurately check the number-of-pieces display during the work without particularly paying attention to the arrangement of the device or the direction of imaging. This significantly improves the workability.

Note that the presentation unit denotes a unit that can present the measurement result to the user and denotes a unit, such as, for example, a display unit, a sound output unit, and a vibration unit, that can present some information to the five senses of the user. A speaker and an amplifier circuit as the sound output unit, an actuator as the vibration unit, and the like can be obviously provided on the body-mounted unit, such as the glass unit 11.

The presentation unit is the on-glass display unit 13 that displays the information on the display surface arranged in front of the eyes of the user in the examples illustrated in the embodiments.

This allows the worker to check the measurement result in the field of view for the work. That is, the worker can naturally view the measurement information in the course of the work without an action of consciously viewing the measurement result, and this is significantly suitable in terms of work efficiency.

The sensor unit 7 that detects grasping of the object by the gripper is provided in the examples described in the embodiments. Examples of the sensor unit 7 that detects grasping of the object by the gripper, such as the hand of the person, the tool, and the robot arm, include an imaging apparatus, a pressure sensor, a thermo tracer, a distance measurement sensor, and the like that detect an image, pressure, temperature information, distance measurement information, and the like.

The information obtained by the sensor unit 7 or the imaging unit 2 can be used to detect the grasping of the object by the gripper, such as, for example, the hand of the person, the tool, and the robot arm, and this allows to appropriately specify the object to be measured and determine the timing for starting the measurement.

The measurement apparatus 1 of the embodiments may also be configured as follows.

The imaging unit 2 may be in a backlight state depending on the work posture in the berry thinning work, and it is desirable that the image sensor in the imaging unit 2 have a dynamic range of equal to or greater than ISO 10000.

In addition, the imaging unit 2 may have an automatic exposure function (Automatic Exposure) and a function that can automatically switch a neutral-density filter (such as a liquid crystal variable ND filter).

An image captured by the imaging unit 2 can be used to improve the measurement accuracy.

Furthermore, to capture moving images without a blur, it is also desirable to use, as the imaging unit 2, an image sensor with a high frame rate or to use an image sensor of a global shutter system.

Furthermore, there may also be a case of work in the rain, and it is desirable that the measurement apparatus 1 have a waterproof structure.

In addition, water repellent finishing may also be applied to the front lens or the cover glass of the imaging unit 2.

Furthermore, it is more preferable to have a function of correcting an aberration in the image caused by raindrops.

The measures against the rain are practically important factors in the case of farming.

In addition, there may be a case in which the crops are shaken due to shaking of the grasped object, and the image is blurred. In this case, the degree of blur can be measured, and a shutter speed corresponding to the degree of blur can be automatically set.

In addition, to provide a uniform amount of exposure when the shutter speed is changed, it is also desirable to have an automatic adjustment function for setting corresponding ISO sensitivity.

Means for using a gyro sensor (angular velocity sensor), an acceleration sensor, or the like to detect the motion of the measurement apparatus 1 to electronically move the pixels according to the amount of detection to correct the blur when the measurement apparatus 1 is vibrated and means for mechanically moving the lens, the image sensor, or the camera module to correct the blur may also be provided.

The measurement apparatus 1 may measure and notify the worker of the sugar content, the estimated price at the time of shipment, the number of pieces per unit area, and the number of pieces to be thinned out, in addition to the number of pieces.

The feature amount is not limited to the number of pieces.

In addition, the work can also be supported by setting an appropriate number of pieces for each bunch, each area in the farm, and the like and notifying the worker of the number of pieces.

In addition, a gyro sensor, an acceleration sensor, a GPS receiver, a geomagnetic sensor, or the like can be used to detect the position of the trajectory of the measurement apparatus 1, and the feature amounts obtained by the measurement apparatus 1 can be mapped in association with the trajectory to make the management of farming efficient.

In addition, a robot can be utilized to measure the number of pieces of each bunch while automatically moving in the farm, and the robot can further perform the berry thinning. The robot can measure the number of pieces at night and notify the worker of the bunches and the number of pieces to be thinned out or the pieces to be thinned out in the next morning. Such a system is also effective.

The measurement start timing and the measurement result may be provided to the worker by sound or video. For example, the timing for starting the measurement is provided to the worker by an electronic sound or the like. This allows the user to figure out the measurement operation of the measurement apparatus 1.

Note that the image analysis unit 4 may execute all or part of the processing steps of the processes in FIGS. 6, 8, 9, 10, 11, and 12 described as processes of the control unit 5. In other words, it is only necessary that the measurement apparatus 1 include a section as a microcomputer and a processor that execute the processes, and the section may be a section as a control unit, a section as an image analysis unit, or another section.

The program of the embodiments is a program for causing, for example, a CPU, a DSP, or a device including the CPU and the DSP to execute the processes of FIGS. 6, 8, 9, 10, 11, and 12.

That is, the program of the embodiments is a program for causing an information processing apparatus to execute the process of specifying the object to be measured based on the detection of the grasping of the object by the gripper and the process of obtaining the measurement result in the measurement process of the feature amount of the specified object to be measured. The program can realize the measurement apparatus 1 and the information processing apparatus 50.

The program can be recorded in advance in an HDD as a recording medium built in a device such as a computer apparatus, a ROM in a microcomputer including a CPU, or the like.

Alternatively, the program can be temporarily or permanently stored (recorded) in a removable recording medium, such as a flexible disk, a CD-ROM (Compact Disc Read Only Memory), an MO (Magnet Optical) disk, a DVD (Digital Versatile Disc), a Blu-ray Disc (registered trademark), a magnetic disk, a semiconductor memory, and a memory card. The removable recording medium can be provided as a so-called packaged software.

In addition, the program can be installed on a personal computer or the like from the removable recording medium or downloaded from a download site through a network, such as a LAN (Local Area Network) and the Internet.

In addition, according to the program, it is suitable to broadly provide the information processing apparatus 50 of the embodiments. For example, the program can be downloaded to a personal computer, a portable information processing apparatus, a portable phone, a gaming device, a video device, a PDA (Personal Digital Assistant), or the like to provide the personal computer or the like as the information processing apparatus 50 that functions as the measurement apparatus 1 or the measurement system of the present disclosure.

Note that the advantageous effects described in the present specification are illustrative only, and the advantageous effects are not limited. There may be other advantageous effects.

Note that the present technique can also be configured as follows.

(1)

A measurement apparatus including:

a measurement object specification unit that executes a process of specifying an object to be measured on the basis of detection of grasping of an object by a gripper; and a measurement unit that obtains a measurement result in a measurement process of a feature amount of the object to be measured specified by the measurement object specification unit.

(2)

The measurement apparatus according to (1), further including:

a presentation control unit that executes a process for presentation based on the measurement result.

(3)

The measurement apparatus according to (1) or (2), in which the measurement process is executed by using a captured image.

(4)

The measurement apparatus according to any one of (1) to (3), in which the measurement process is executed on the basis of detection of grasping of the object by the gripper.

(5)

The measurement apparatus according to any one of (1) to (3), in which the measurement process is executed on the basis of detection of grasping of the object and moving of the object by the gripper.

(6)

The measurement apparatus according to any one of (1) to (3), in which the measurement process is executed on the basis of detection of grasping of the object by the gripper and a predetermined action other than the grasping.

(7)

The measurement apparatus according to any one of (1) to (6), in which the measurement process is executed by using images of a plurality of frames captured in a period in which the object to be measured is moved.

(8)

The measurement apparatus according to any one of (1) to (7), in which the measurement object specification unit executes a process of setting, as the object to be measured, the object grasped and moved by the gripper.

(9)

The measurement apparatus according to any one of (1) to (8), further including:

a target setting unit that sets a target value of the feature amount, in which the target setting unit obtains a difference value of the feature amount measured in the measurement process and the target value.

(10)

The measurement apparatus according to (9), further including:

a presentation control unit that executes a process for presenting the difference value.

(11)

The measurement apparatus according to (5) or (8), in which the movement is a rotational movement.

(12)

The measurement apparatus according to any one of (1) to (11), in which the gripper is one of a hand of a person, a tool operated by the person, and an automatically operated robot arm.

(13)

The measurement apparatus according to any one of (1) to (12), in which the object as the object to be measured is a crop.

(14)

The measurement apparatus according to any one of (1) to (13), in which the measurement object specification unit executes a process of setting, as the object to be measured, a bunch of grapes in which a branch is grasped by the gripper, and in the measurement process, the number of pieces is measured as the feature amount of the bunch of grapes set as the object to be measured.

(15)

The measurement apparatus according to (3) or (7), further including an imaging unit that captures an image to be used in the measurement process.

(16)

The measurement apparatus according to any one of (1) to (15), further including:

an imaging unit that captures an image to be used in the measurement process; and a presentation unit that presents the measurement result, in which the imaging unit and the presentation unit are arranged on a body-mounted unit.

(17)

The measurement apparatus according to (16), in which the presentation unit is a display unit that displays information on a display surface arranged in front of eyes of a user.

(18)

The measurement apparatus according to any one of (1) to (17), in which a sensor unit that detects grasping of the object by the gripper is provided.

(19)

A measurement method executed by an information processing apparatus, the measurement method including:

a process of specifying an object to be measured on the basis of detection of grasping of an object by a gripper; and a process of obtaining a measurement result in a measurement process of a feature amount of the specified object to be measured.

(20)

A program causing an information processing apparatus to execute:

a process of specifying an object to be measured on the basis of detection of grasping of an object by a gripper; and a process of obtaining a measurement result in a measurement process of a feature amount of the specified object to be measured.

(21)

A measurement method executed by an information processing apparatus, the measurement method including:

a process of specifying a bunch of grapes to be measured on the basis of detection of grasping of the bunch of grapes by a gripper; and a process of starting to measure the number of pieces of the specified bunch of grapes.

(22)

A measurement method executed by an information processing apparatus, the measurement method including:

a process of specifying a bunch of grapes grasped by a gripper; and a process of measuring the number of pieces of the specified bunch of grapes along with rotation of the specified bunch of grapes.

REFERENCE SIGNS LIST

1 Measurement apparatus, 1A Measurement terminal, 2 Imaging unit, 3 Image signal processing unit, 4 Image analysis unit, 5 Control unit, 5a Measurement object specification unit, 5b Measurement unit, 5c Presentation control unit, 5d Target setting unit, 6 Operation unit, 7 Sensor unit, 8 Display control unit, 9 Display unit, 10 Storage unit, 11 Glass unit, 12 Camera, 13 On-glass display unit, 14 Cord, 15 Control unit, 16 Communication unit, 21 Hand, 22, 23, 24 Grape, 22A Branch, 22B Bunch, 25 Number-of-pieces display, 26 Target display, 27 Status display, 28 Situation display, 29 Captured image display, 30 Berry thinning section display, 50 Information processing apparatus, 51 Communication terminal, 52 Network, 53 Cloud server, 54 AI engine, 60 Imaging apparatus

The invention claimed is:

1. A measurement apparatus comprising:

a measurement object specification unit that executes a process of specifying an object to be measured on a basis of detection of grasping of an object by a gripper; and a measurement unit that obtains a measurement result in a measurement process of a feature amount of the object to be measured specified by the measurement object specification unit.

2. The measurement apparatus according to claim 1, further comprising:

a presentation control unit that executes a process for presentation based on the measurement result.

3. The measurement apparatus according to claim 1, wherein the measurement process is executed by using a captured image.

4. The measurement apparatus according to claim 1, wherein the measurement process is executed on a basis of detection of grasping of the object by the gripper.

5. The measurement apparatus according to claim 1, wherein the measurement process is executed on a basis of detection of grasping of the object and moving of the object by the gripper.

6. The measurement apparatus according to claim 1, wherein the measurement process is executed on a basis of detection of grasping of the object by the gripper and a predetermined action other than the grasping.

7. The measurement apparatus according to claim 1, wherein the measurement process is executed by using images of a plurality of frames captured in a period in which the object to be measured is moved.

8. The measurement apparatus according to claim 1, wherein the measurement object specification unit executes a process of setting, as the object to be measured, the object grasped and moved by the gripper.

9. The measurement apparatus according to claim 1, further comprising:

a target setting unit that sets a target value of the feature amount, wherein the target setting unit obtains a difference value of the feature amount measured in the measurement process and the target value.

10. The measurement apparatus according to claim 9, further comprising:

a presentation control unit that executes a process for presenting the difference value.

11. The measurement apparatus according to claim 5, wherein the movement is a rotational movement.

12. The measurement apparatus according to claim 1, wherein the gripper is one of a hand of a person, a tool operated by the person, and an automatically operated robot arm.

13. The measurement apparatus according to claim 1, wherein the object as the object to be measured is a crop.

14. The measurement apparatus according to claim 1, wherein the measurement object specification unit executes a process of setting, as the object to be measured, a bunch of grapes in which a branch is grasped by the gripper, and in the measurement process, the number of pieces is measured as the feature amount of the bunch of grapes set as the object to be measured.

15. The measurement apparatus according to claim 3, further comprising:

an imaging unit that captures an image to be used in the measurement process.

16. The measurement apparatus according to claim 1, further comprising:

an imaging unit that captures an image to be used in the measurement process; and a presentation unit that presents the measurement result, wherein the imaging unit and the presentation unit are arranged on a body-mounted unit.

17. The measurement apparatus according to claim 16, wherein the presentation unit is a display unit that displays information on a display surface arranged in front of eyes of a user.

18. The measurement apparatus according to claim 1, wherein
a sensor unit that detects grasping of the object by the gripper is provided.

19. A measurement method executed by an information processing apparatus, the measurement method comprising:
a process of specifying an object to be measured on a basis of detection of grasping of an object by a gripper; and
a process of obtaining a measurement result in a measurement process of a feature amount of the specified object to be measured.

20. A program causing an information processing apparatus to execute:
a process of specifying an object to be measured on a basis of detection of grasping of an object by a gripper; and
a process of obtaining a measurement result in a measurement process of a feature amount of the specified object to be measured.

21. A measurement method executed by an information processing apparatus, the measurement method comprising:
a process of specifying a bunch of grapes to be measured on a basis of detection of grasping of the bunch of grapes by a gripper; and
a process of starting to measure the number of pieces of the specified bunch of grapes.

22. A measurement method executed by an information processing apparatus, the measurement method comprising:
a process of specifying a bunch of grapes grasped by a gripper; and
a process of measuring the number of pieces of the specified bunch of grapes along with rotation of the specified bunch of grapes.

* * * * *